US006335195B1

(12) United States Patent
Rodgers et al.

(10) Patent No.: US 6,335,195 B1
(45) Date of Patent: *Jan. 1, 2002

(54) METHOD FOR PROMOTING HEMATOPOIETIC AND MESENCHYMAL CELL PROLIFERATION AND DIFFERENTIATION

(75) Inventors: Kathleen E. Rodgers, Long Beach; Gere S. DiZerega, Pasadena, both of CA (US)

(73) Assignee: Maret Corporation, Newport Beach, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/012,400

(22) Filed: Jan. 23, 1998

Related U.S. Application Data

(60) Provisional application No. 60/036,507, filed on Jan. 28, 1997, provisional application No. 60/046,859, filed on May 8, 1997, provisional application No. 60/063,684, filed on Oct. 28, 1997, provisional application No. 60/063,910, filed on Oct. 31, 1997, provisional application No. 60/065,612, filed on Nov. 18, 1997, and provisional application No. 60/066,593, filed on Nov. 26, 1997.

(51) Int. Cl.$^7$ .............................. C12N 5/00; C12N 5/02; A61K 38/00; C07K 7/06
(52) U.S. Cl. ........................... 435/377; 514/16; 514/21; 530/316; 530/329
(58) Field of Search ........................... 435/377; 514/16, 514/21; 530/316, 329

(56) References Cited

U.S. PATENT DOCUMENTS

| | | | |
|---|---|---|---|
| 5,015,629 A | 5/1991 | diZerega | 514/12 |
| 5,486,359 A | 1/1996 | Caplan et al. | 424/93.7 |
| 5,629,292 A | 5/1997 | Rodgers et al. | 514/16 |
| 5,693,616 A | 12/1997 | Krstenansky et al. | 514/12 |
| 5,716,935 A | 2/1998 | diZerega et al. | 514/16 |

FOREIGN PATENT DOCUMENTS

| | | |
|---|---|---|
| WO | WO 95/08337 | 3/1985 |
| WO | WO 95/08565 | 3/1995 |
| WO | WO 96/14858 | 5/1996 |
| WO | WO 96/39164 | 12/1996 |
| WO | WO 97/34627 | 9/1997 |

OTHER PUBLICATIONS

Toshio Kato, et al., (1993), *Radiation Medicine*, "New Modality of Radiation Therapy Under Increased Tumor Oxygen Tension with Angiotensin II: A Pilot Study"11:(3, pp. 86–90.

Chen, Z, et al., EMBO J. 12(3):1161–1167, 1993.*

Itoh, N., et al., Science. 247:324–327, Jan. 1990.*

Moskow, J.J., et al., Molec. Cell. Biol. 15(10):5434–5443, Oct. 1995.*

Zhang, Y–W, et al., Molec. Cell. Biol. 17(7):4133–4145, Jul. 1997.*

Mrug et al., "Angiotensin II stimulates proliferation of normal early erythroid progenitors." J. Clinical Investigation 100 (9):2310–2314 (1997).

Rodgers et al., Histologic alterations in dermal repair after thermal injury effects of topical angiotensin II. *J. Burn Care Rehabil.* 18:381–388 (1997).

DeCherney et al., Expression of cyclin protein after thermal skin injury in a guinea pig model. *J. Burn Care Rehabil.* 18:292–298 (1997).

Hunt, T.K. et al., Coagulation and macrophage stimulation of angiogenesis and wound healing. In The surgical wound, pp. 1–18, ed. F. Dineen & G. Hildrick–Smith (Lea & Febiger, Philadelphia: (1981).

Kunapuli and Kumar, Molecular cloning of human angiotensinogen cDNA and evidence for the presence of its mRNA in rat heart. *Circulation Research* 60:786–790 (1987).

Clouston et al., Molecular cloning of the mouse angiotensinogen gene. *Genomics* 2:240–248 (1988).

Kageyama et al., Primary structure of human preangiotensinogen deduced from the cloned cDNA sequence. *Biochemistry* 23:3603–3609 (1984).

Ohkubo et al., Cloning and sequence analysis of cDNA for rat angiotensinogen. *Proc. Natl. Acad. Sci.* 80:2196–2200 (1983).

Berk et. al., Angiotensin II–stimulated protein synthesis in cultured vascular smooth muscle cells. *Hypertension* 13:305–14 (1989).

Kawahara, et al., Angiotensin II induces expression of the c–fos gene through protein kinase C activation and calcium ion mobilization in cultured vascular smooth muscle cells. *BBRC* 150:52–9 (1988).

Naftilan, et al., Induction of platelet–derived growth factor A–chain and c–myc gene expressions by angiotensin II in cultured rat vascular smooth muscle cells. *J. Clin. Invest.* 83:1419–23 (1989).

(List continued on next page.)

Primary Examiner—David Saunders
Assistant Examiner—Mary Beth Tung
(74) Attorney, Agent, or Firm—David S. Harper; McDonnell Boehnen Hulbert & Berghoff

(57) ABSTRACT

The present invention provides methods, improved cell culture medium and kits for promoting hematopoietic and mesenchymal stem and lineage-specific cell proliferation and differentiation by growth in the presence of angiotensinogen, angiotensin I (AI); AI analogues, AI fragments and analogues thereof, angiotensin II (AII), AII analogues, AII fragments or analogues thereof or AII $AT_2$ type 2 receptor agonists, either alone or in combination with other growth factors and cytokines.

13 Claims, 17 Drawing Sheets

OTHER PUBLICATIONS

Figure 17:
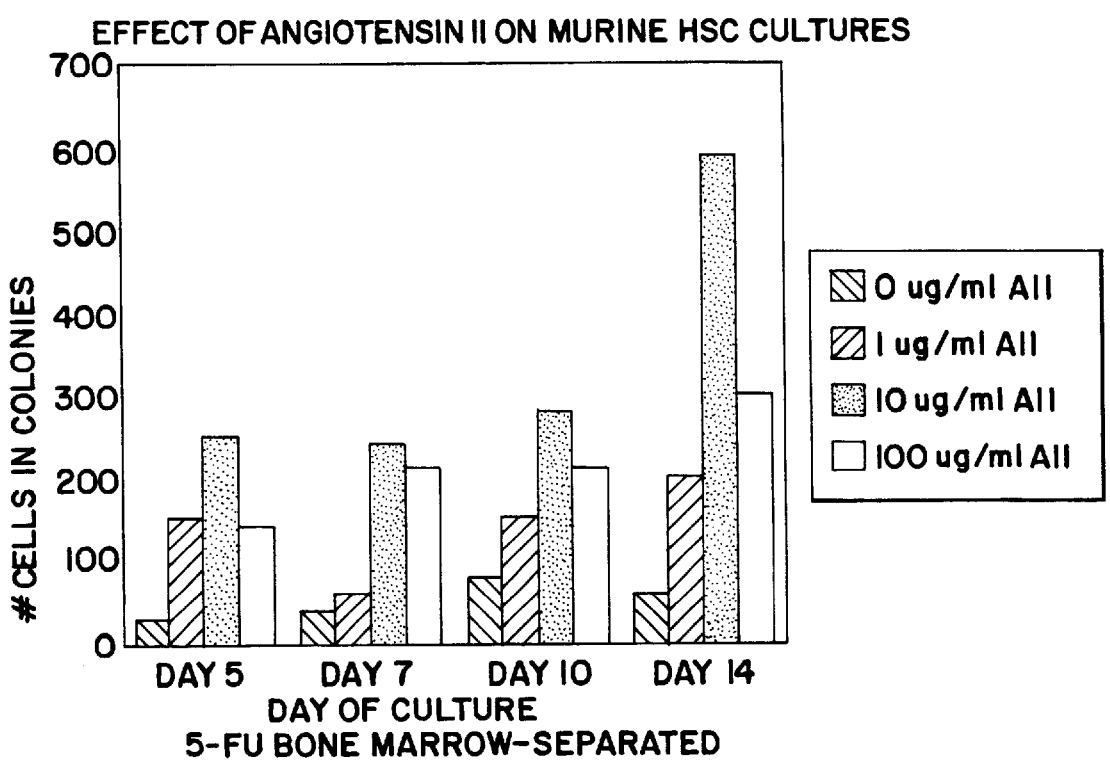
Figure 18:
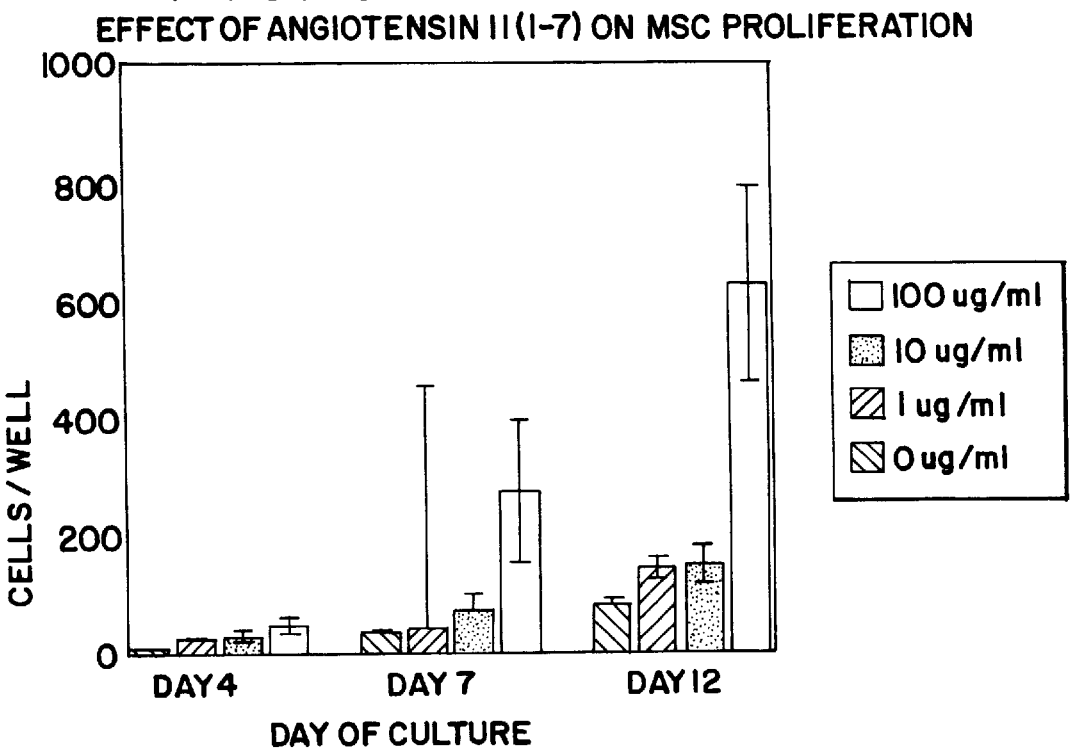
Figure 19:
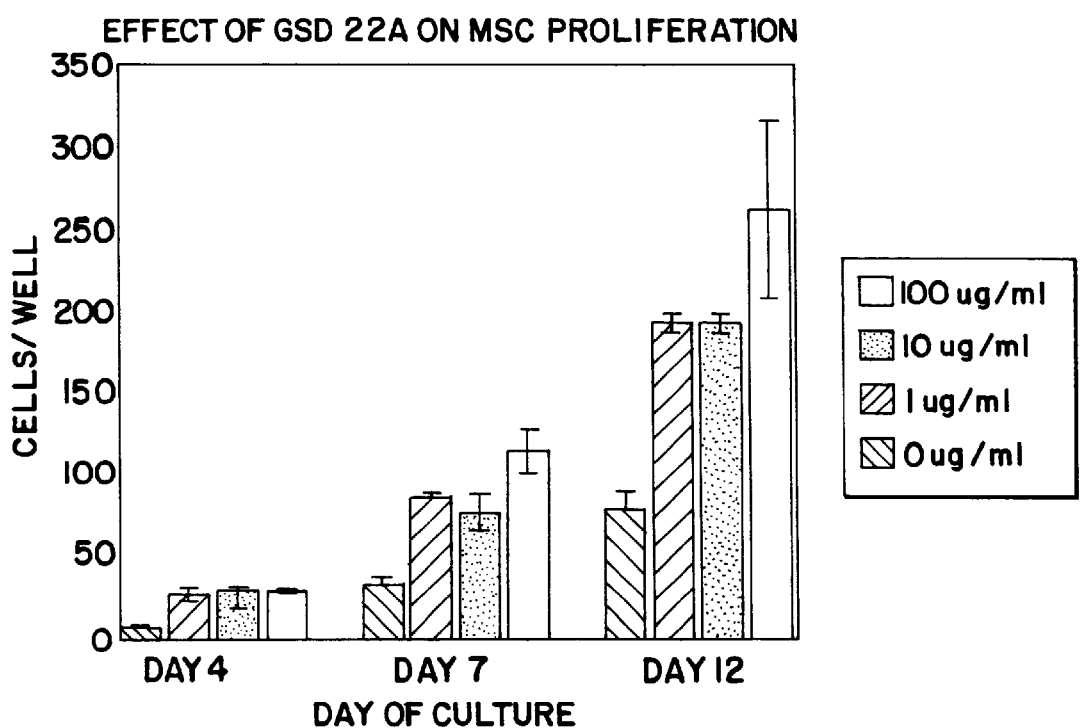
Figure 20:
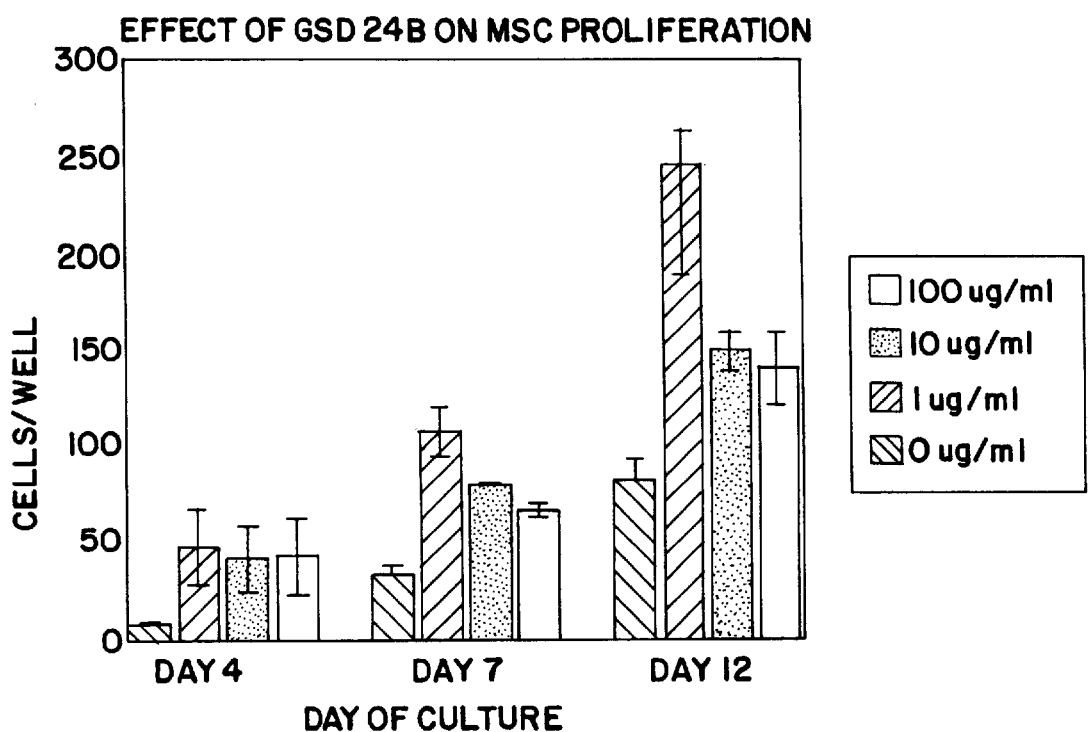
Figure 21:
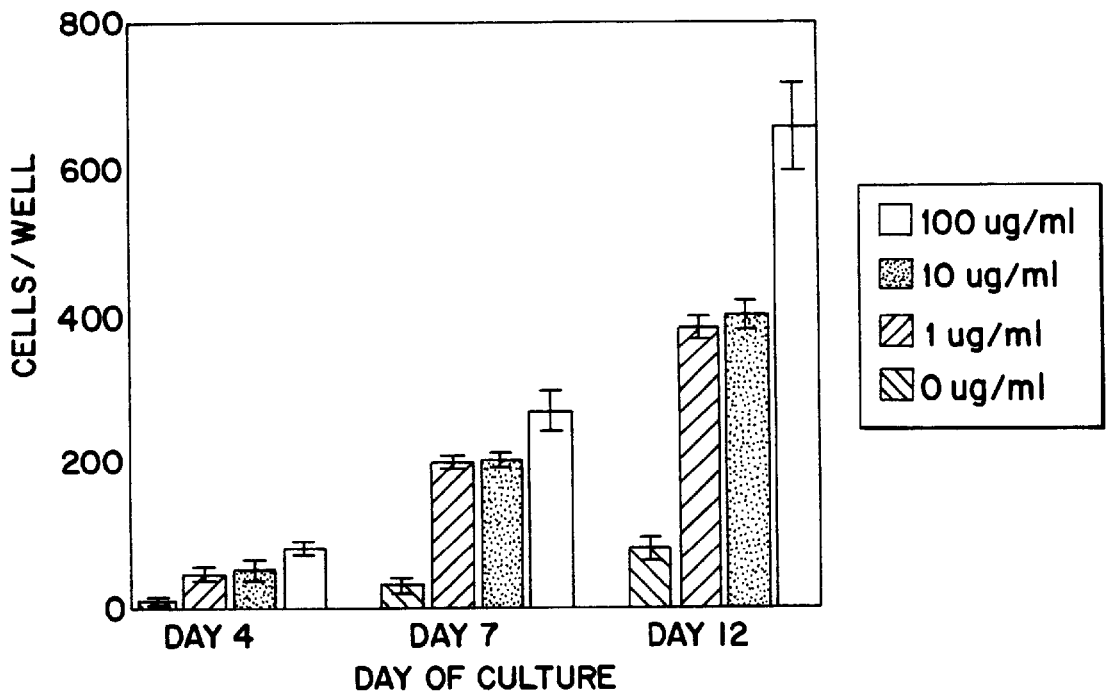

Taubman et al., Angiotensin II induces c-fos mRNA in aortic smooth muscle. *J. Biol. Chem.* 264:526–530 (1989).

Nakahara, et al., Identification of three types of PDGF–A chain gene transcripts in rabbit vascular smooth muscle and their regulated expression during development and by angiotensin II. *BBRC* 184:811–8 (1992).

Stouffer and Owens, Angiotensin II–induced mitogenesis of spontaneously hypertensive rat–derived cultured smooth muscle cells is dependent on autocrine production of transforming growth factor beta. *Circ. Res.* 70:820 (1992).

Wolf, et al., Angiotensin II stimulates the proliferation and biosynthesis of type I collagen in cultured murine mesangial cells. *Am. J. Pathol.* 140:95–107 (1992).

Bell and Madri, Influence of the angiotensin system on endothelial and smooth muscle cell migration. *Am. J. Pathol.* 137:7–12 (1990).

Fernandez, et al., Neovascularization produced by angiotensin II. *J. Lab. Clin. Med.* 105:141 (1985).

LeNoble, et al., Angiotensin II stimulates angiogenesis in the chorio–allantoic membrane of the chick embryo. *Eur. J. Pharmacol.* 195:305–6 (1991).

Powell, et al., Inhibitors of angiotensin–converting enzyme prevent myointimal proliferation after vascular injury. *Science* 245:186–8 (1989).

Powell, et al., The proliferative response to vascular injury is suppressed by angiotensin–converting enzyme inhibition. *J. Cardiovasc. Pharmacol.* 16:S42–9 (1991).

Capron, et al., Effect of ramipril, an inhibitor of angiotensin converting enzyme, on the response of rat thoracic aorta to injury with a balloon catheter. *J. Cardiovasc. Pharmacol.* 18:207–11 (1991).

Osterrieder, et al., Role of angiotensin II in injury–induced neointima formation in rats. *Hypertension* 18(Supp) II60–64 (1991).

Daemen et al., Angiotensin II induces smooth muscle cell proliferation in the normal and injured rat arterial wall. *Circ. Res.* 68:450–6 (1991).

Schelling, et al., Effects of angiotensin II and angiotensin II antagonist saralasin on cell growth and renin in 3T3 and SV3T3 cells. *J. Cell. Physiol.* 98:503–14 (1979).

Campbell–Boswell and Robertson, Effects of angiotensin II and vasopressin on human smooth muscle cells in vitro. *Exp. Mol. Pathol.* 35:265–76 (1981).

Paquet, et al., Angiotensin II–induced proliferation of aortic myocytes in spontaneously hypertensive rats. *J. Hyperten.* 8:565–72 (1990).

Naftilan, The role of angiotensin II in vascular smooth muscle cell growth. *J. Cardiovas. Pharmacol.* 20:S37–40 (1992).

Gibbons, et al., Vascular smooth muscle cell hypertrophy vs. hyperplasia. *J. Clin. Inv.* 90:456–61 (1992).

Bell, et al., Autcrine angiotensin system regulation of bovine aortic endothelial cell migration and plasminogen activator involves modulation of proto–oncogene $pp60^{c-src}$ expression. *J. Clin. Inv.* 89:315–20 (1992).

Wolf, et al., Intracellular signaling of transcription and secretion of type IV collagen after angiotensin II–induced cellular hypertrophy in cultured proximal tubular cells. *Cell. Reg.* 2:219–27 (1991).

Zhou, et al., Angiotensin II–mediated stimulation of collagen synthesis in cultured cardiac fibroblasts. *FASEB. J.* 6:A1914 (5661) (1992).

Pfeilschifter, et al., Angiotensin II stimulation of phospholipase D in rat renal mesangial cells is mediated by the AT1 receptor subtype. *Eur. J. Pharmacol.* 225:57–62 (1992).

Jaiswal, et al., Stimulation of endothelial cell prostaglandin production by angiotensin peptides. *Hypertension* 19(Supp. II):II–49–II–55 (1992).

Edwards and Stack, Angiotensin II inhibits glomerular adenylate cylcase via the angiotensin II receptor subtype 1. *J. Pharmacol. Exper. Ther.* 266:506–510 (1993).

Jaiswal, et al., Differential regulation of prostaglandin synthesis by angiotensin peptides in aortic smooth muscle cells: Subtypes of angiotensin receptors involved. *J. Pharmacol. Exper. Ther.* 265:664–673 (1991).

Jaiswal, et al., Subtype 2 angiotensin receptors mediate prostaglandin synthesis in human astrocytes. *Hypertension* 17:1115–1120 (1991).

Portsi, et al., Release of nitric oxide by angiotensin–(1–7) from porcine coronary endothelium: implications for a novel angiotensin receptor. *Br. J. Pharmacol.* 111:652–654 (1994).

Janiak et al., Role of angiotensin subtype 2 receptor in neointima formation after vascular injury. *Hypertension* 20:737–45 (1992).

Prescott et al., Angiotensin–converting enzyme inhibitor versus angiotensin II, AT1 receptor antagonist. *Am. J. Pathol.* 139:1291–1296 (1991).

Kauffman, et al., Losartan, a nonpeptide angiotensin II (Ang II) receptor antagonist, inhibits neointima formation following balloon injury to rat carotid arteries. *Life Sci.* 49:223–228 (1991).

Viswanathan et al., Expression of angiotensin II AT2 receptors in the rat skin during experimental wound healing. *Peptides* 13:783–786 (1992).

Kimura et al., Chanes in skin angiotensin II receptors in rats during wound healing. *BBRC* 187:1083–1090 (1992).

Regoli et al., Pharmacology of angiotensin. *Pharmacological Reviews* 26:69 (1974).

Frosch and Kligman, The chamber–scarification test for irritancy. Contact Dermatitis 2(6): 314–324 (1976).

Emerson, Ex vivo expansion of hematopoietic precursors, progenitors, and stem cells: The next generation of cellular therapeutics. *Blood* 87:3082–3088 (1996).

Larochelle et al., Identification of primitive human hematopoietic cells capable of repopulating NOD/SCID mouse bone marrow: Implications for gene therapy. *Nature Medicine* 2:1329–1337, (1996).

Bruder et al., Mesenchymal stem cells in bone development, bone repair, and skeletal regeneration therapy. *J. Cellul. Biochem.* 56:283–294 (1994).

Caplan, The mesengenic process. In *Clinics in Plastic Surgery* 21:429–435 (1994).

Caplan et al., Mesenchymal stem cells and tissue repair. In *The Anterior Cruciate Ligament: Current and Future Concepts,* ed. D.W. Jackson, Raven Press, Ltd. NY pp. 405–417 (1993).

Lazarus et al., Ex vivo expansion and subsequent infusion of human bone marrow–derived stromal progenitor cells (mesenchymal progenitor cells): Implications for therapeutic use. *Bone Marrow Transplantation* 16:557–564 (1995).

Allay et al., Retroviral transduction of marrow derived mesenchymal precursors. *Blood* 82:477A (1993).

Berardi et al., Basic fibroblast growth factor mediates its effects on committed myeloid progenitors by direct action and has no effect on hematopoietic stem cells. *Blood* 86:2123–2129 (1995).

Fritsch et al., The composition of CD34 subpopulations differs between bone marrow, blood and cord blood. *Bone Marrow Transplantation* 17:169–178 (1996).

Lemieux et al., Characterizations and purification of a primitive hematopoietic cell type in adult mouse marrow capable of lymphomyeloid differentiation in long term marrow "switch" cultures. *Blood* 86:1339–1347 (1995).

Speth and Kim, Discrimination of two angiotensin II receptor subtypes with a selective agonist analogue of angiotensin II, p–aminophenylalanine$^6$ angiotensin II. *BBRC* 169:997–1006 (1990).

Catalioto et al., Angiotensins induce the release of prostacyclin from rabbit vas deferens: Evidence for receptor heterogeneity. *Eur. J. Pharmacol.* 256:93–97 (1994).

Bryson et al., Induction of the angiotensin AT2 receptor subtype expression by differentiation of the neuroblastoma x glioma hybrid, NG–108–15. *Eur. J. Pharmacol.* 225:119–127 (1992).

Bodine et al., Bone marrow collected 14 days after in vivo administration of granulocyte colony–stimulating factor and stem cell factor to mice has 10–fold more repopulating ability than untreated bone marrow. *Blood* 88:89–97 (1996).

Johnson and Dorshkind, Stromal cells in myeloid and lymphoid long–term bone marrow cultures can support multiple hemopoietic lineages and modulate their production of hemopoietic growth factors. *Blood* 68(6):1348–1354 (1986).

Bab et al., Kinetics and differentiation of marrow stromal cells in diffusion chambers in vivo. *J. Cell Sci.* 84:139–151 (1986).

Benayahu et al., Bone marrow–derived stromal cell line expressing osteoblastic phenotype in vitro and osteogenic capacity in vivo. *J. Cellular Physiology* 140:1–7 (1989).

Rodgers and Xiong, Contribution of mast cell mediators to alterations in macrophage function after malathion administration. *Fundamental and Applied Toxicology* 33:100–108 (1996).

Rodgers et al., Effects of tolmetin sodium dihydrate on normal and postsurgical peritoneal function. *International Journal of Immunopharmacology* 10:111–120 (1988).

Rodgers, Measurement of the respiratory burst of leukocytes for immunotoxicologic analysis. In: *Modern Methods in Immunotoxicology* (ed. G. Burleson), Wiley Liss 2:67–77 (1995).

Traycoff et al., Ex vivo expansion of murine hematopoietic progenitor cells generates classes of expanded cells possessing different levels of bone marrow repopulating potential. *Experimental Hematology* 24:299–306 (1996).

Alcorn and Holyoake, Ex vivo expansion of hematopoietic progenitor cells. *Blood Reviews* 10:167–176 (1996).

Prockop, Marrow stromal cells as stem cells for nonhematopoietic tissues. *Science* 276:71–74 (1997).

Talmadge et al., Immunological attributes of cytokine mobilized peripheral blood stem cells and recovery following transplantation. *Bone Marrow Transplantation* 17:101–109 (1996).

Holyoake et al., Ex vivo expansion with stem cell factor and interleukin–11 augments both short–term recovery post-transplant and the ability to serially transplant marrow. *Blood* 87:4589–4595 (1996).

Takaku, Cytokines and bone marrow transplantation. *J. Cancer Res. Clin. Oncol.* 121:701–709 (1995).

* cited by examiner

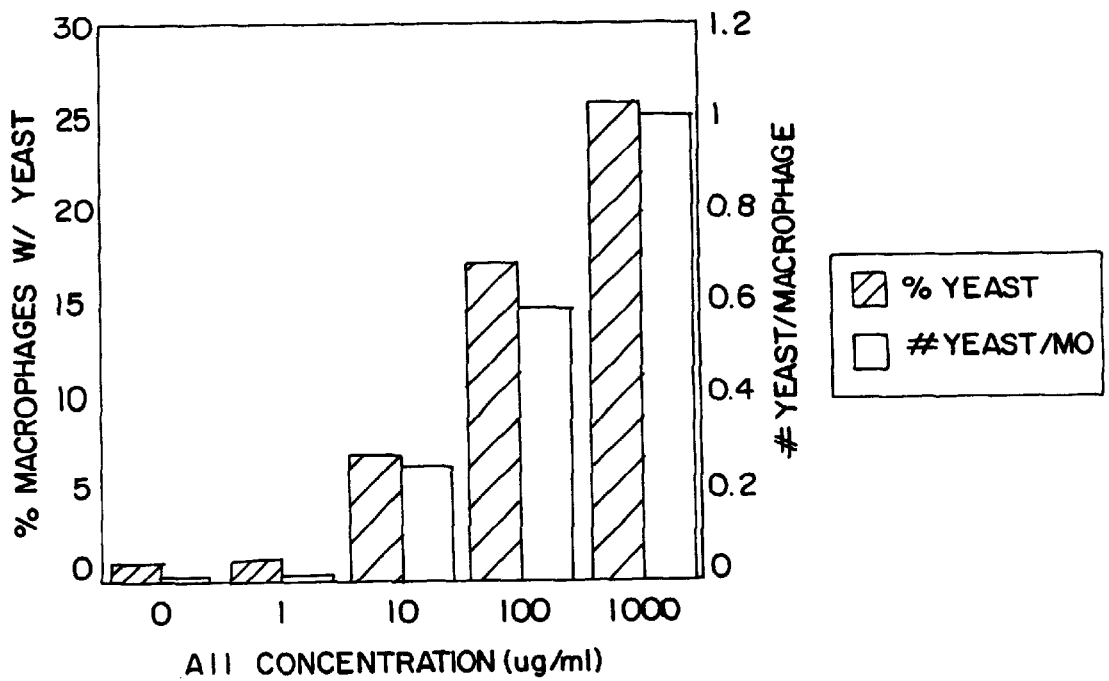
FIG. 1  EFFECT OF AII ON PHAGOCYTIC CAPABILITY OF MURINE MACROPHAGES
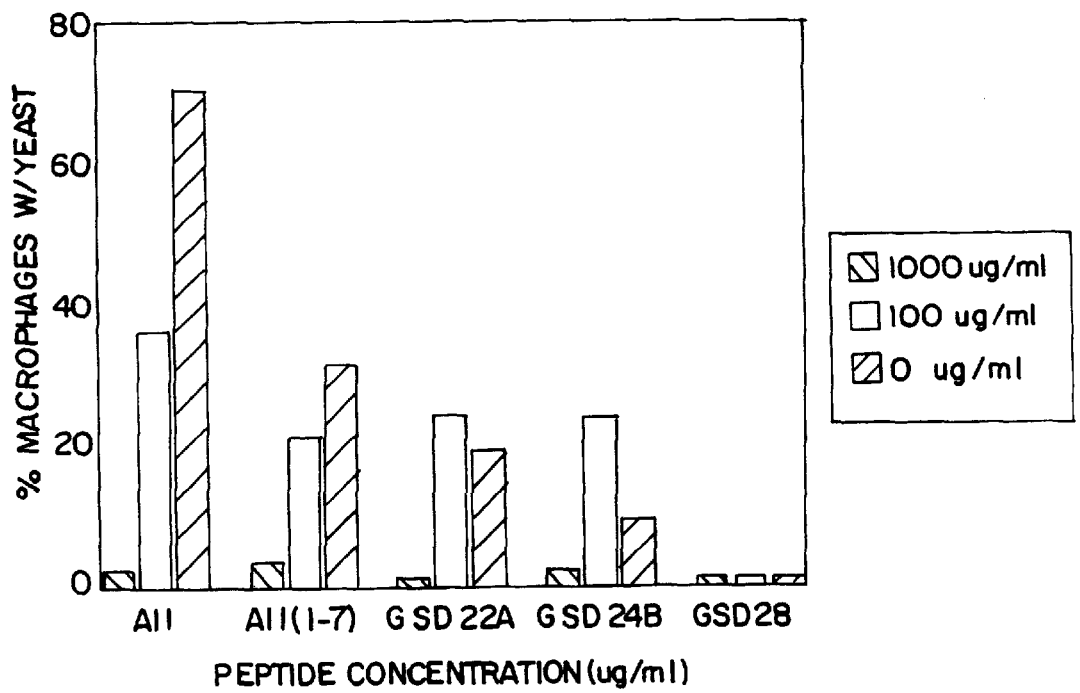
FIG. 2  EFFECT OF AII ON PHAGOCYTIC CAPABILITY OF RAT MACROPHAGES

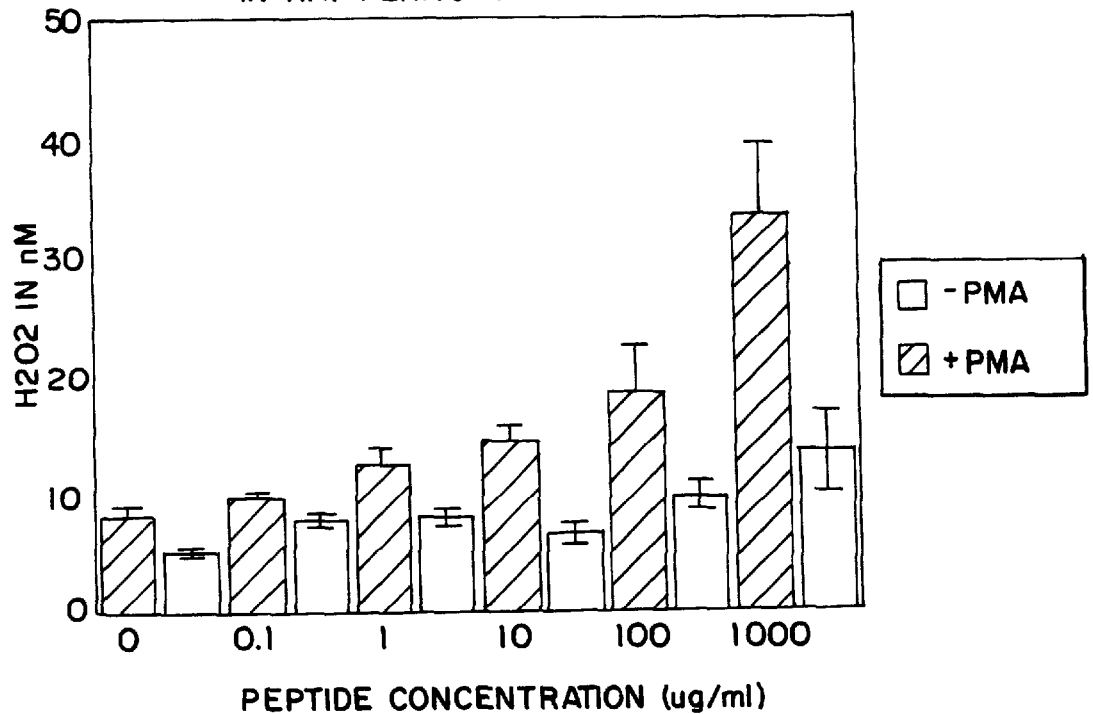
FIG. 3 EFFECT OF ANGIOTENSIN II ON RESPIRATORY BURST FUNCTION IN RAT PERITONEAL MACROPHAGES
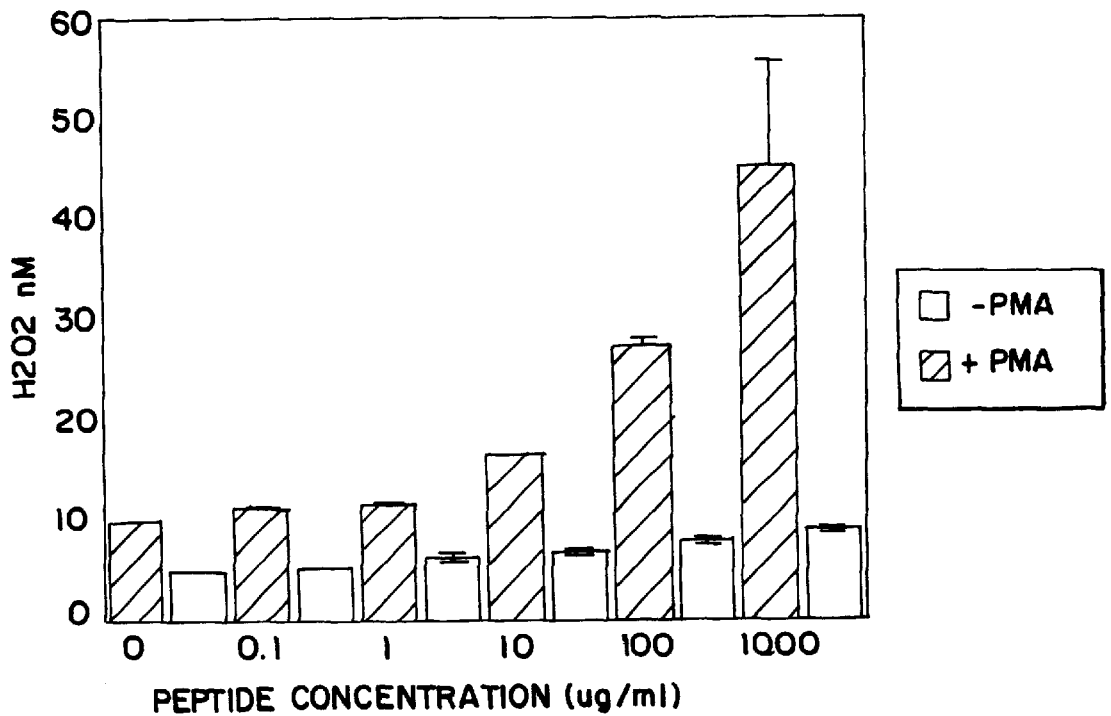
FIG. 4 EFFECT OF ANGIOTENSIN ON RESPIRATORY BURST FUNCTION IN HUMAN PBMC FIG. 5 EFFECT OF ANGIOTENSIN I-7 ON RESPIRATORY BURST FUNCTION IN RAT PERITONEAL MACROPHAGE
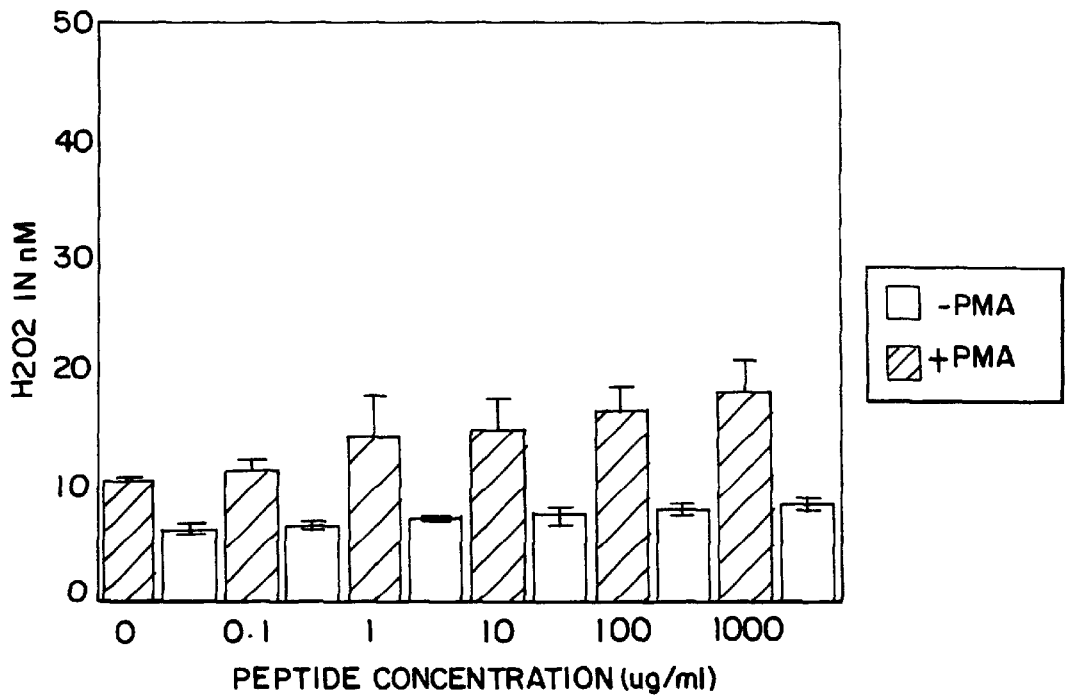
FIG. 6 EFFECT OF GSD 248 ON RESPIRATORY BURST FUNCTION IN RAT PERITONEAL MACROPHAGE
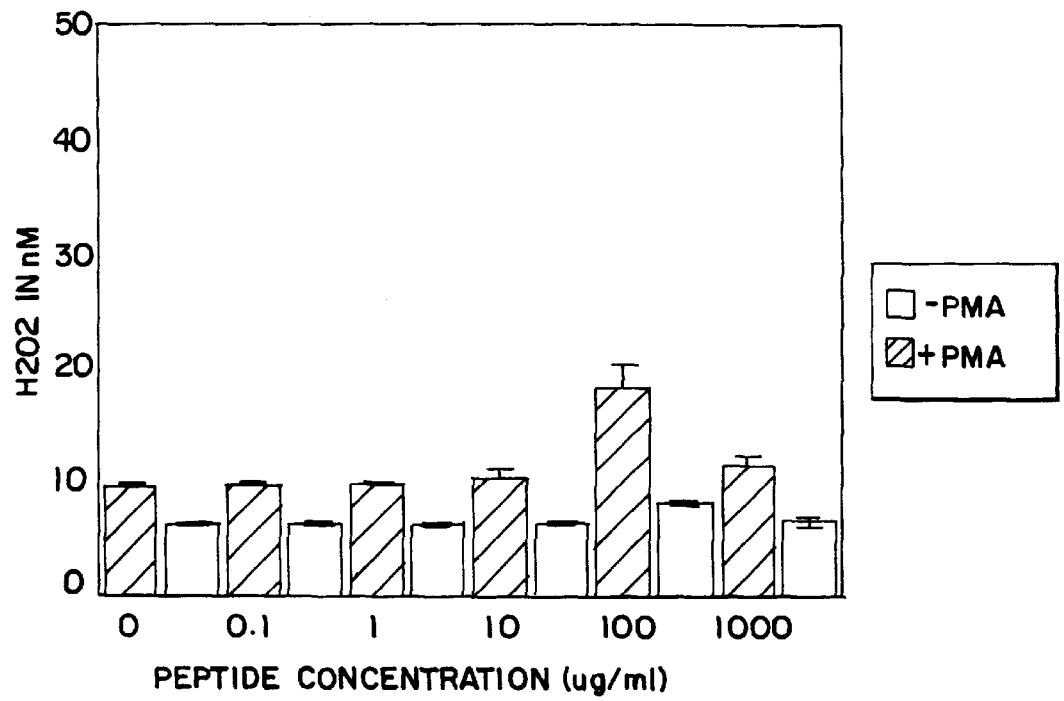

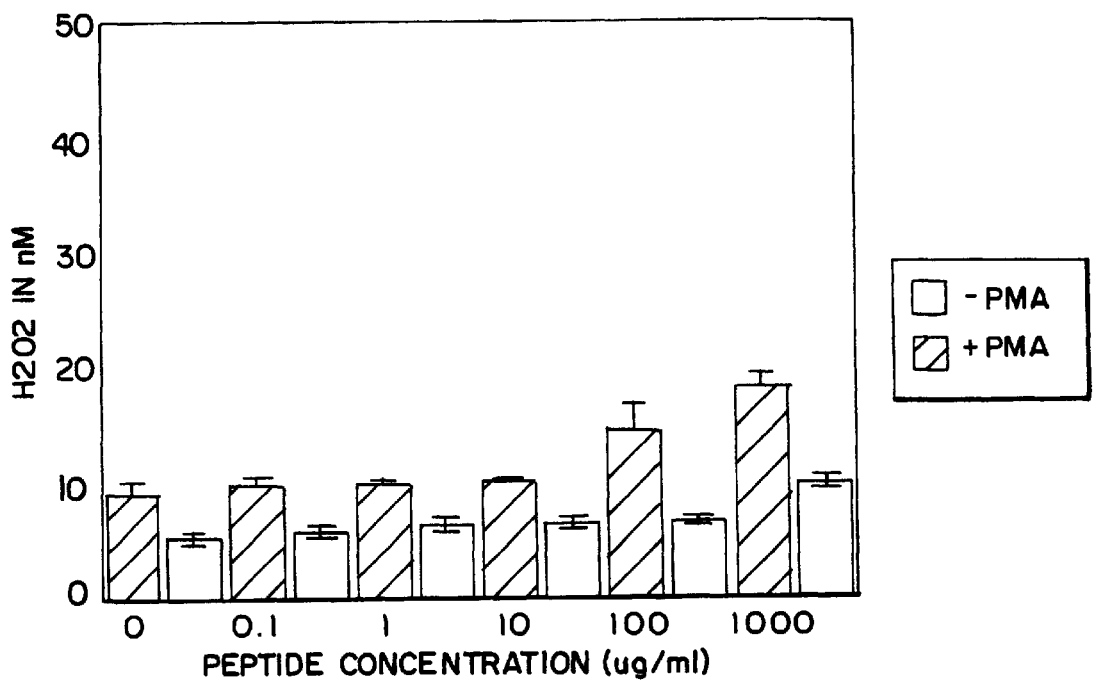
FIG. 7 EFFECT OF GSD 22A ON RESPIRATORY BURST FUNCTION IN RAT PERITONEAL MACROPHAGES
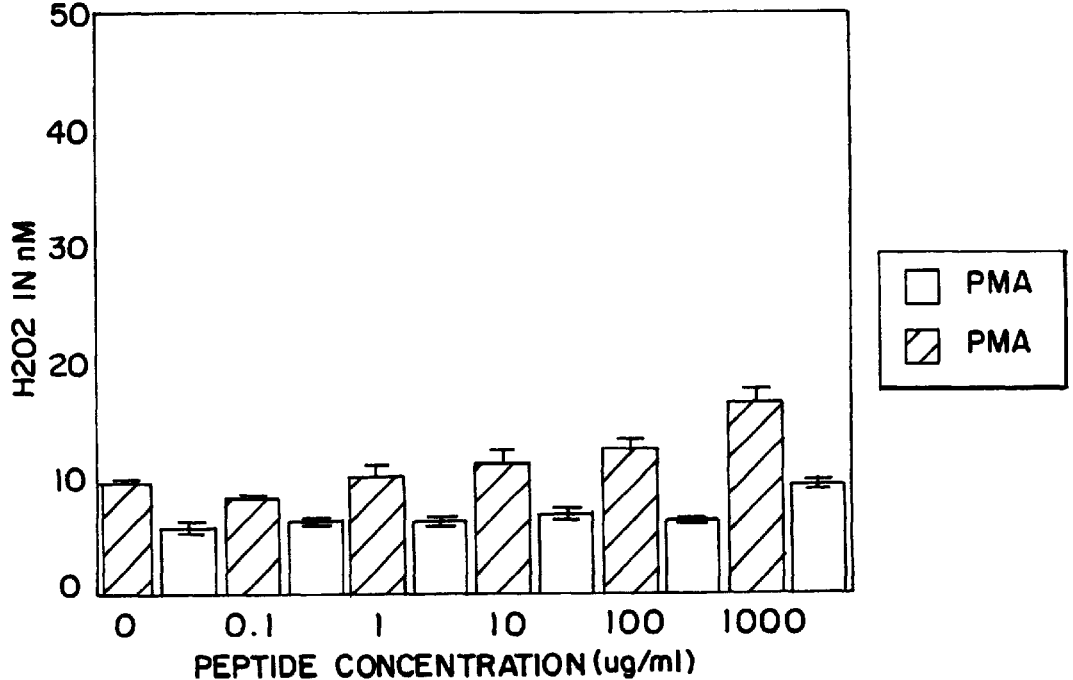
FIG. 8 EFFECT OF GSD 28 ON RESPIRATORY BURST FUNCTION IN RAT PERITIONEAL MACROPHAGE FIG. 9 EFFECT OF AII ON PROLIFERATION IN RESPONSE TO POKEWEED MITOGEN
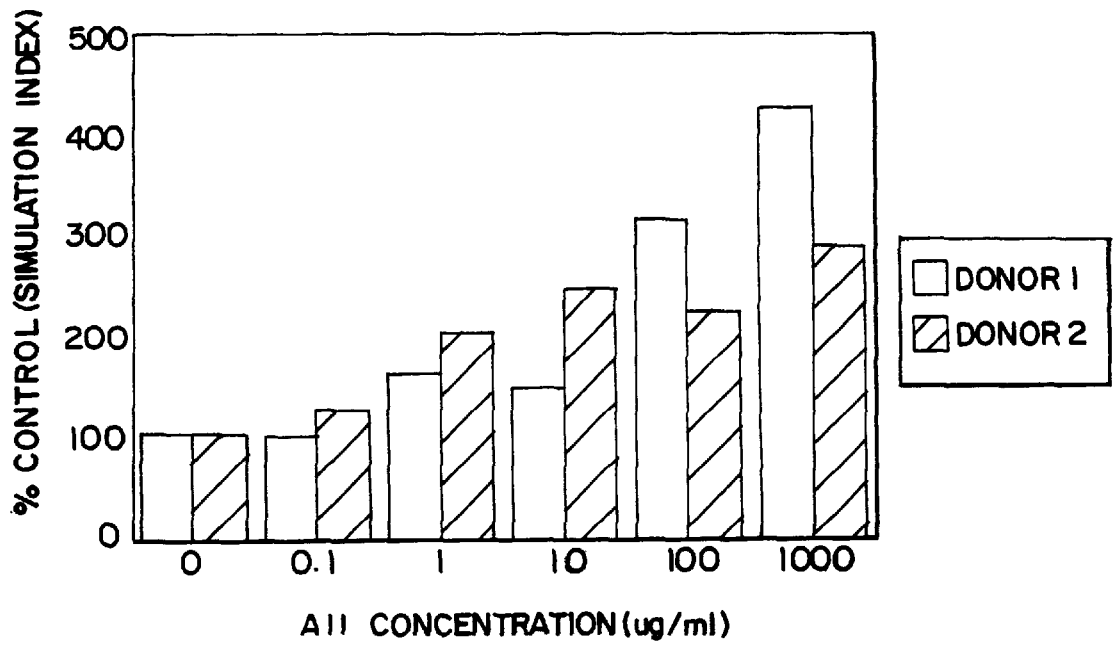
FIG. 10 EFFECT OF AII ON RAT BONE MARROW CULTURES SERUM 3
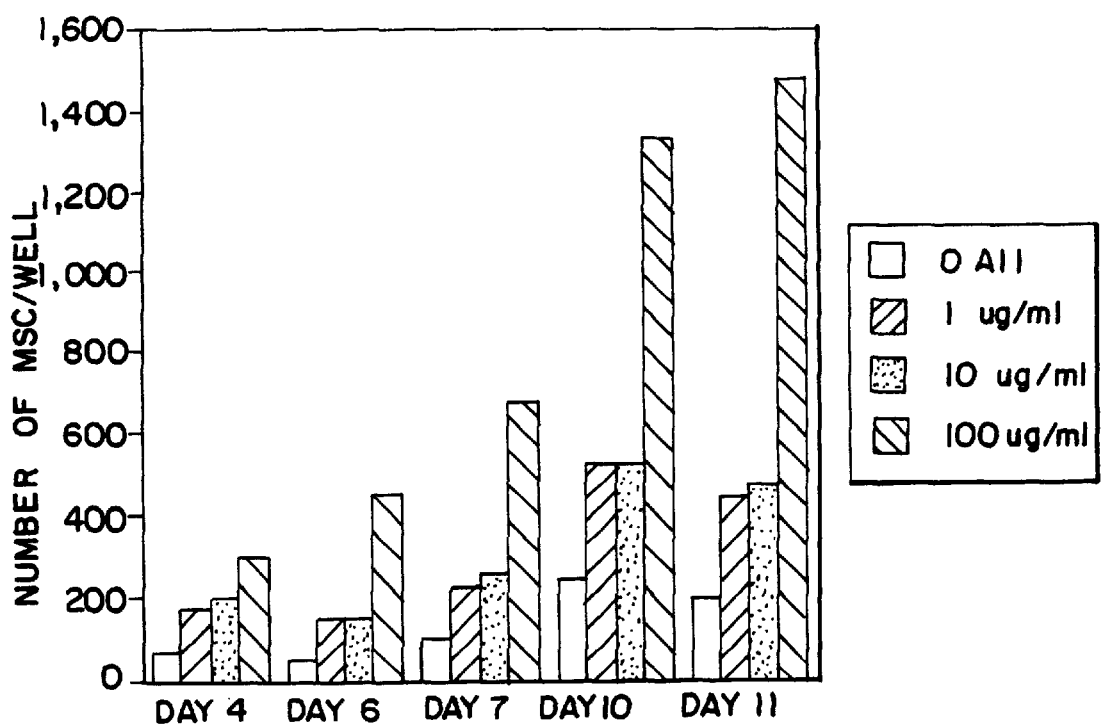

FIG. 11 EFFECT OF AII ON RAT BONE MARROW CULTURES SERUM 3 9/5/97 CULTURE
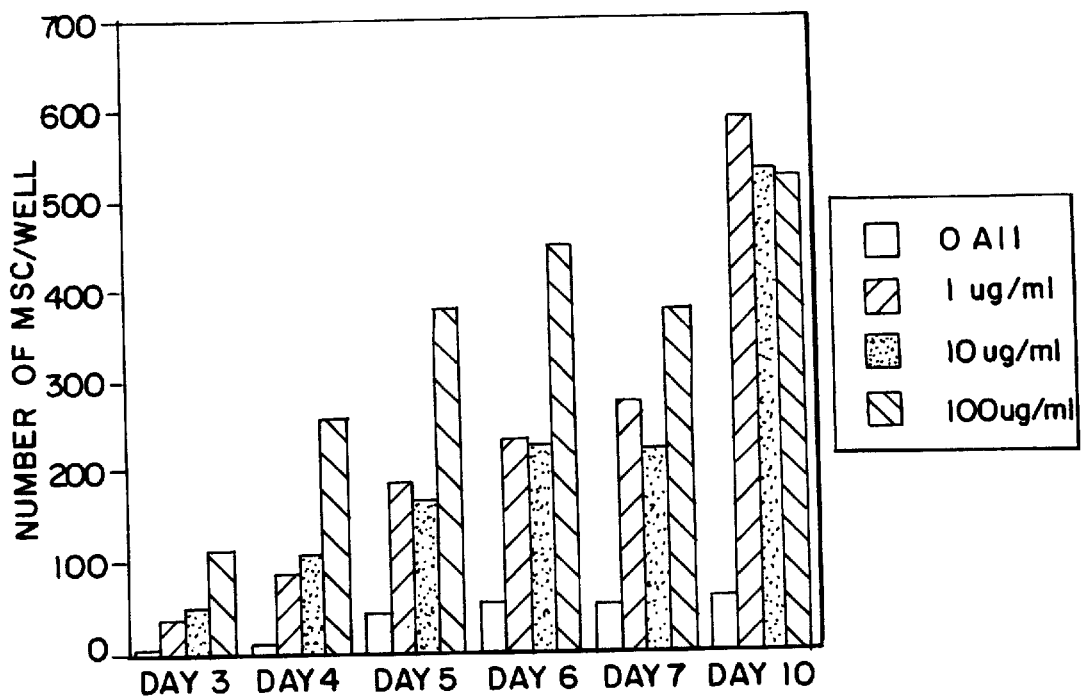
FIG. 12 EFFECT OF ANGIOTENSIN II ON MURINE HSC CULTURES
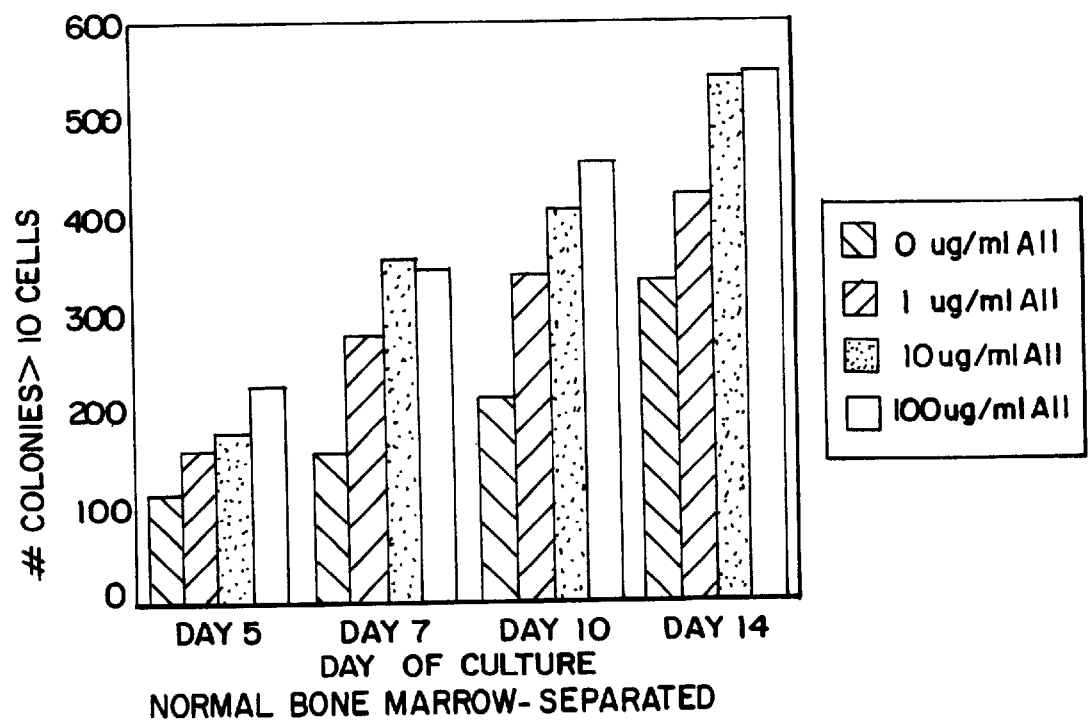
NORMAL BONE MARROW- SEPARATED EFFECT OF ANGIOTENSIN II ON MURINE HSC CULTURES
FIG. 13
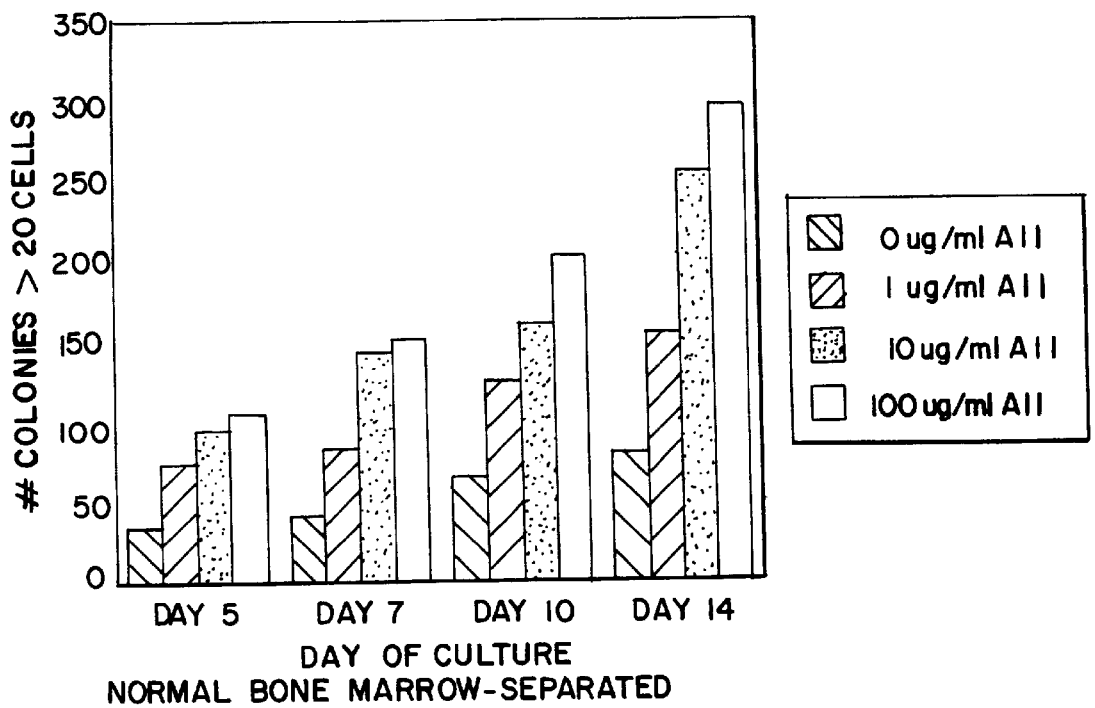
NORMAL BONE MARROW-SEPARATED
FIG. 14  EFFECT OF ANGIOTENSIN II ON MURINE HSC CULTURES
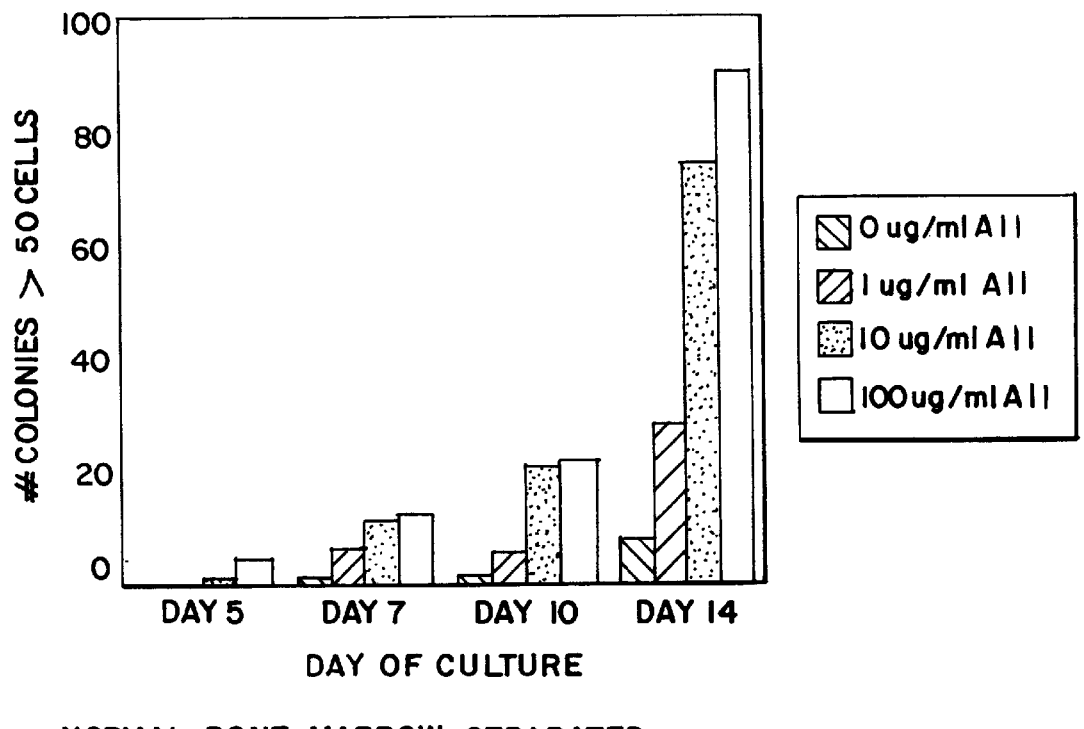
NORMAL BONE MARROW-SEPARATED

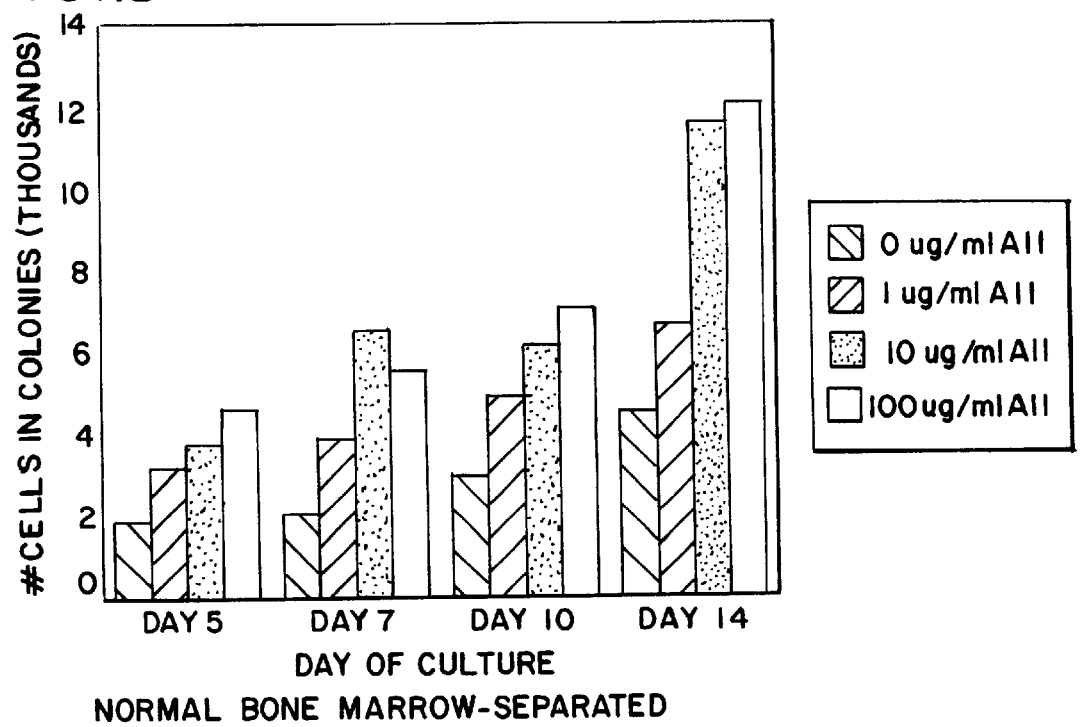
FIG. 15 EFFECT OF ANGIOTENSIN II ON MURINE HSC CULTURES
NORMAL BONE MARROW-SEPARATED
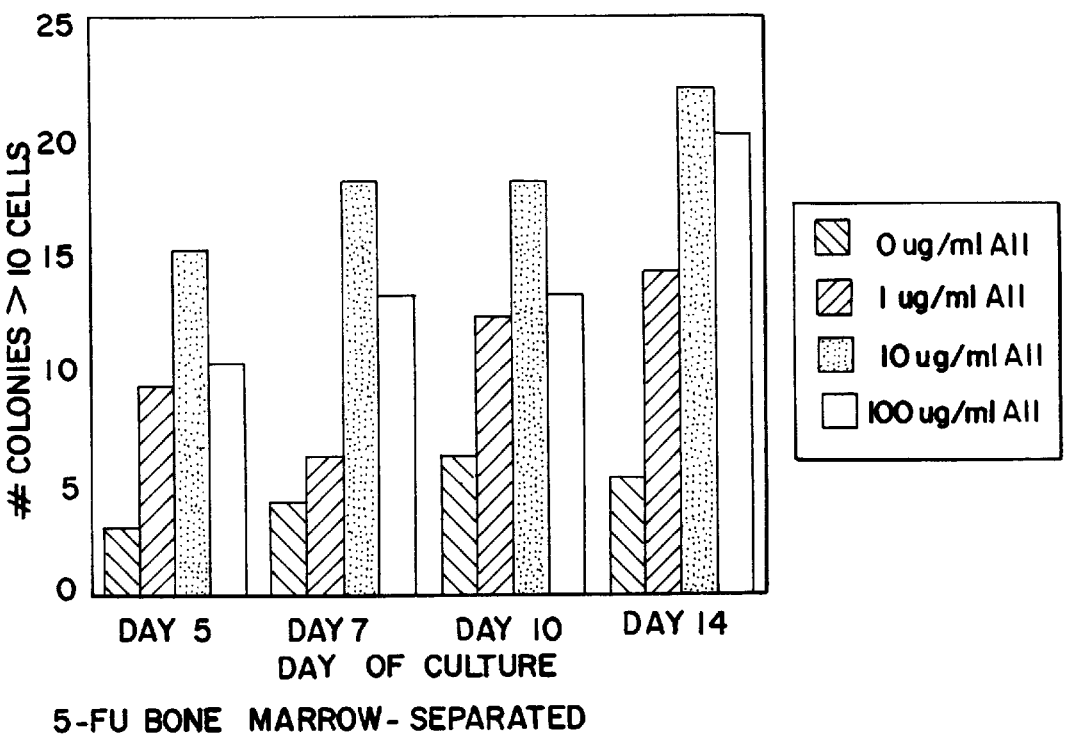
FIG. 16 EFFECT OF ANGIOTENSIN II ON MURINE HSC CULTURES
5-FU BONE MARROW-SEPARATED

EFFECT OF GSD 28 ON MSC PROLIFERATION

EXPRESSION OF ALKALINE PHOSPHATASE
BY MESENCHYMAL STEM CELLS

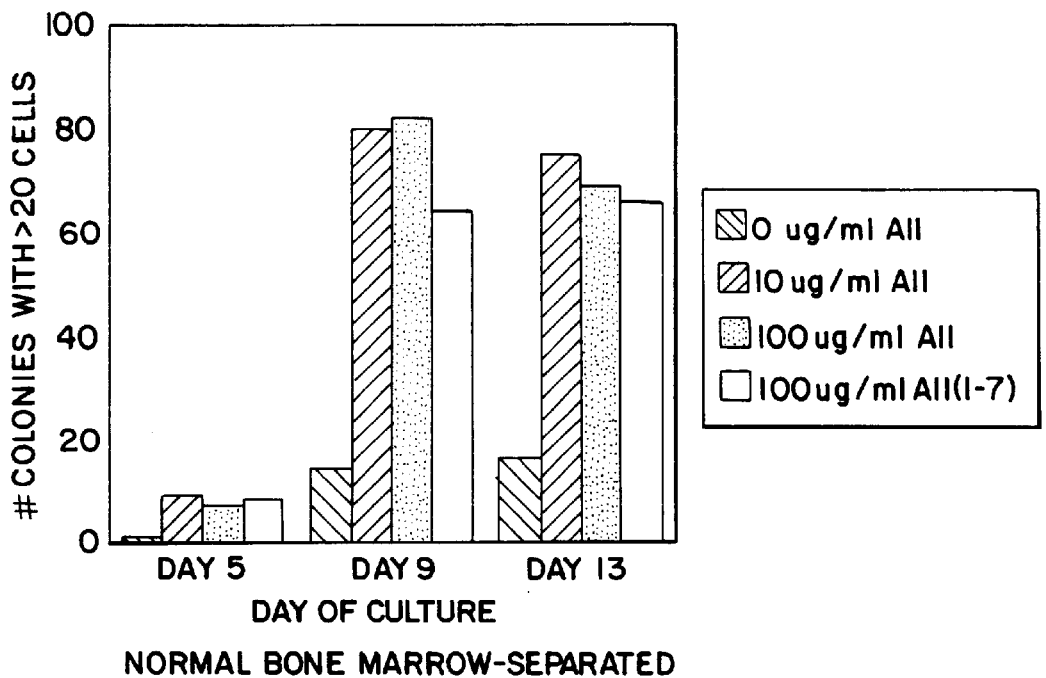
FIG. 27 EFFECT OF ANGIOTENSIN II/ANALOGUES WITHOUT CSF ON MURINE HPC CULTURE
NORMAL BONE MARROW-SEPARATED
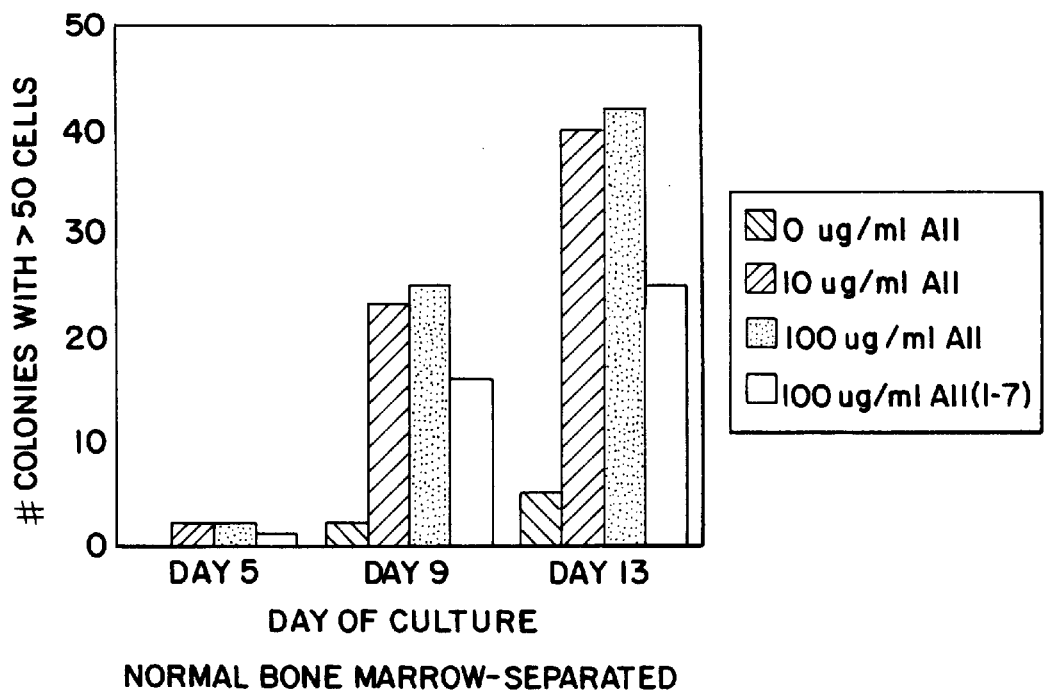
FIG. 28 EFFECT OF ANGIOTENSIN II/ANALOGUES WITHOUT CSF ON MURINE HPC CULTURE
NORMAL BONE MARROW-SEPARATED

EFFECT OF ANGIOTENSIN II/ANALOGUES WITHOUT CSF ON MURINE HPC CULTURE

NORMAL BONE MARROW-SEPARATED

EFFECT OF ANGIOTENSIN II/ANALOGUES WITHOUT CSF ON MURINE HPC CULTURE

NORMAL BONE MARROW-SEPARATED

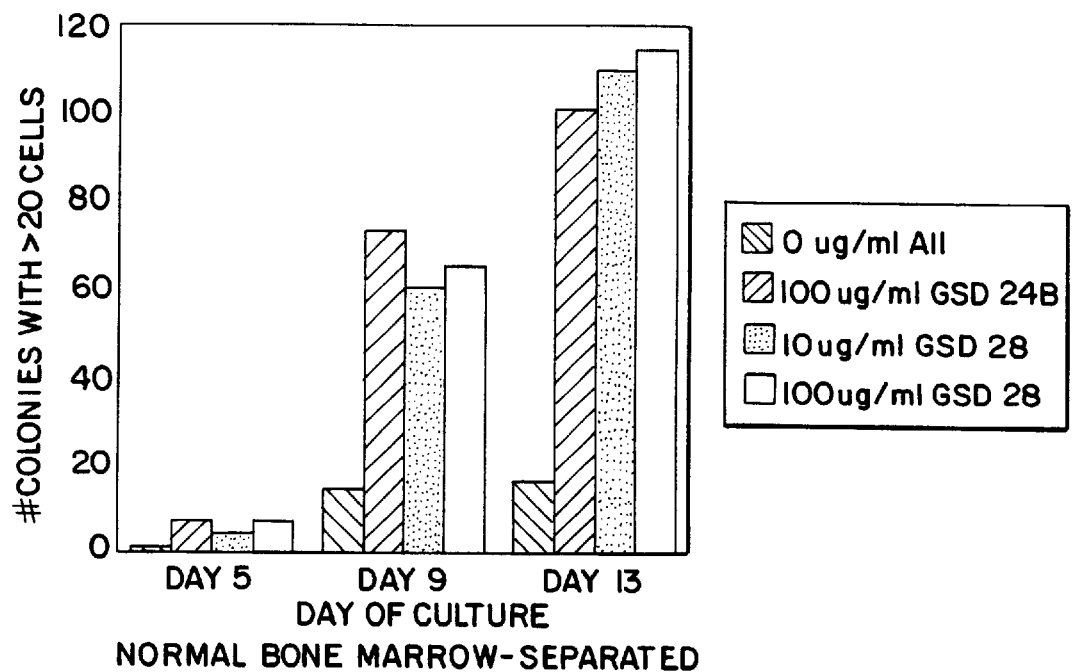
FIG. 31 EFFECT OF ANGIOTENSIN II/ANALOGUES WITHOUT CSF ON MURINE HPC CULTURE
NORMAL BONE MARROW-SEPARATED
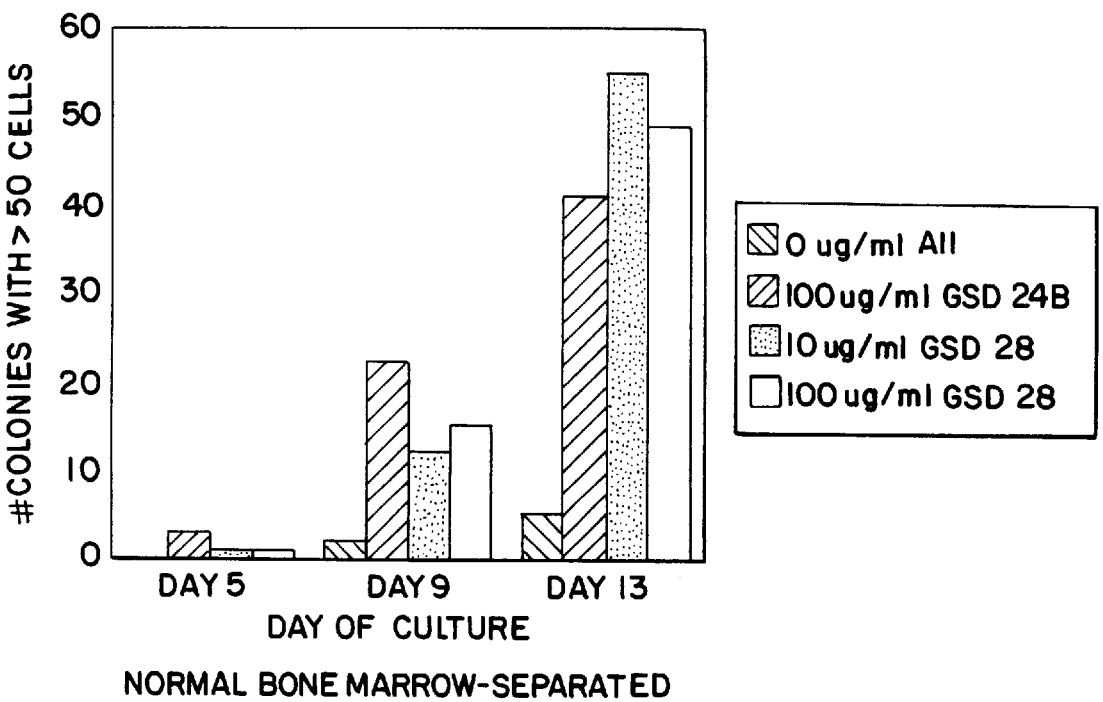
FIG. 32 EFFECT OF ANGIOTENSIN II/ANALOGUES WITHOUT CSF ON MURINE HPC CULTURE
NORMAL BONE MARROW-SEPARATED

METHOD FOR PROMOTING HEMATOPOIETIC AND MESENCHYMAL CELL PROLIFERATION AND DIFFERENTIATION

CROSS REFERENCE

This application is a Continuation-In-Part of U.S. Provisional Application No. 60/036,507, filed Jan. 28, 1997, No. 60/046,859, filed May 8, 1997; No. 60/063,684 filed Oct. 28, 1997; No. 60/063,910 filed Oct. 31, 1997; No. 60/065,612 filed Nov. 18, 1997; and No. 60/066,593 filed Nov. 26, 1997.

FIELD OF THE INVENTION

This present invention relates to methods and kits for use in accelerating the proliferation and differentiation of hematopoietic and mesenchymal cells.

BACKGROUND OF THE INVENTION

Bone marrow contains pluripotent stem cells that are capable of reconstituting either the hematopoietic system or a wide range of mesenchymal tissues. The mechanisms by which hematopoietic and mesenchymal stem cells produce a range of lineage-specific cell types are quite dissimilar.

a. The Hematopoietic System

The hematopoietic system is composed of a multitude of cell generations ranging from the terminally differentiated to very primitive hematopoietic lineage-specific cells, including a multipotent, self-renewing hematopoietic stem cell with long-term repopulating capability (HPC). (Traycoff, et al., *Experimental Hematology* 24:299–306, 1996). HPC are pluripotent lineage-specific cells that possess the ability to terminally differentiate into hematopoietic lineage-specific cells (HLSC). Hematopoiesis is an ongoing process, and therefore HPC must provide a continuous source of HLSC, which in turn can differentiate into red cells, platelets, monocytes, granulocytes and lymphocytes. (Prockop, *Science* 276:71–74, 1997). HPC proliferate either by "self-renewal", to produce HPC-type progeny cells, or with accompanying differentiation, to produce HLSC. (Traycoff, et al., supra).

HPC transplantation therapy has been successful for a variety of malignant and inherited diseases and also provides myelopoietic support for patients undergoing high-dose chemotherapy or radiotherapy. (Emerson, *Blood* 87:3082–3088, 1996). However, stem cell transplantation has been limited by several features. First, acquiring a sufficient quantity of stem cells to achieve benefit after transfusion requires either extensive, operative bone marrow harvests or extensive pheresis procedures. (Emerson, supra). Next, even under these circumstances, only a limited number of useful cells is obtained. Finally, mature blood cell regeneration after transfusion is slow, so that little direct therapeutic benefit is seen for periods of 1 to 3 weeks. (Emerson, supra).

The development of in vitro culture techniques for hematopoietic cells combined with technologies for isolating relatively pure populations of HPC and HLSC has made possible their ex vivo expansion. (Alcorn and Holyoake, *Blood Reviews* 10:167–176, 1996, which is incorporated by reference herein). Successful ex vivo expansion of HPC, both by self-renewal and proliferation with differentiation, promises many clinical benefits, such as reduction of the number and duration of leucapheresis procedures required for autologous transplantation, thus reducing the risk of disease contamination in the apheresis products. (Alcorn and Holyoake, supra). Furthermore, ex vivo expansion may render inadequate HPC populations in peripheral blood and umbilical cord blood sufficient for autologous transplantation and adult allogeneic transplantation respectively. Finally, ex vivo expansion of HPC will greatly increase their utility as gene therapy vehicles. (Alcorn and Holyoake, supra). Similarly, ex vivo expansion of HLSC promises substantial clinical benefits, such as re-infusion of expanded populations of myeloid precursor cells to reduce the period of obligate neutropenia following autologous transplantation, the generation of natural killer cells for use in adoptive immunotherapy protocols, generation of megakaryocyte precursors to alleviate post-transplant-associated thrombocytopenia and more efficient generation of delivery systems for gene therapy. (Alcorn and Holyoake, supra).

Human bone marrow, umbilical cord blood, and peripheral blood lineage-specific cells mobilized by chemotherapy and/or cytokine treatment have been shown to be effective sources of HPC for transplantation following the administration of high-dose therapy to treat malignancy. (Holyoake, et al., *Blood* 87:4589–4595, 1996). Whatever the source of hematopoietic cells, most studies have used cultured cell populations selected on the basis of HPC-specific surface antigens, such as CD34. These cells can be readily obtained by a number of techniques. (Alcorn and Holyoake, supra). The results of several clinical trials using ex vivo expanded hematopoietic cells suggests that a fairly small number of HPC cultured ex vivo under appropriate conditions can initiate hematologic reconstitution. (Emerson, supra).

Survival and proliferation of HPC in ex vivo culture requires a combination of synergizing growth factors; the choice of cytokine/growth factor combination and culture system used will largely determine the fate of cells used to initiate the culture. (Alcorn and Holyoake, supra). In vivo, blood cell production is thought to be regulated locally by interactions of hematopoietic stem cells with a variety of cell-bound and secreted factors produced by adjacent bone marrow stromal cells. (Alcorn and Holyoake, supra). The addition of growth factors and cytokines to the culture medium is intended to compensate for the absence of stroma-associated activities. Growth factors and cytokines that have been shown to increase production of HPC (in various combinations) include granulocyte colony-stimulating factor (G-CSF), granulocyte/macrophage colony stimulating factor (GM-CSF), stem cell factor (SCF), macrophage colony-stimulating factor (M-CSF), and interleukins 1, 3, 6, and 11 (Reviewed in Takaku, *J. Cancer Res. Clin. Oncol.* 121:701–709, 1995; Holyoake, et al., supra). Conversely, inclusion of macrophage inhibitory protein-1α (MIP-1α), tumor necrosis factor a (TNF-α) or transforming growth factor β (TGFβ) in most expansion cultures reported to date results in decreased HPC and HLSC yields. (Emerson, supra).

A great deal of effort has gone into defining the optimal conditions for ex vivo culture of hematopoietic cells. Improved methods that increase of ex vivo proliferation rate of HPC will greatly increase the clinical benefits of HPC transplantation. This is true both for increased "self-renewal", which will provide a larger supply of HPC capable of reconstituting the entire hematopoietic system, and for proliferation with differentiation, which will provide a larger supply of lineage-specific cells. Similarly, methods that increase in vivo proliferation of HPC will enhance the utility of HPC transplantation therapy by rapidly increasing local concentrations of HPC (and HLSC) in the bone marrow. Furthermore, methods that result in the differentiation of HPC and HLSC are useful in providing populations of specific cell types for use in cell therapy.

Transfection of mammalian HPC has been accomplished. (Larochelle, et al., *Nature Medicine* 2:1329–1337, 1996).

Thus, methods that increase the proliferation of HPC and HLSC are also useful in rapidly providing a large population of transfected cells for use in gene therapy.

b. Mesenchymal Stem Cells

Mesenchymal stem cells (MSC) are pluripotent progenitor cells that possess the ability to differentiate into a variety of mesenchymal tissue, including bone, cartilage, tendon, muscle, marrow stroma, fat and dermis as demonstrated in a number of organisms, including humans (Bruder, et al., *J. Cellul. Biochem.* 56:283–294 (1994). The formation of mesenchymal tissues is known as the mesengenic process, which continues throughout life, but proceeds much more slowly in the adult than in the embryo (Caplan, *Clinics in Plastic Surgery* 21:429–435 (1994). The mesengenic process in the adult is a repair process but involves the same cellular events that occur during embryonic development (Reviewed in Caplan, 1994, supra). During repair processes, chemoattraction brings MSC to the site of repair where they proliferate into a mass of cells that spans the break. These cells then undergo commitment and enter into a specific lineage pathway (differentiation), where they remain capable of proliferating. Eventually, the cells in the different pathways terminally differentiate (and are no longer able to proliferate) and combine to form the appropriate skeletal tissue, in a process controlled by the local concentration of tissue-specific cytokines and growth factors (Caplan, 1994, supra).

Recently, it has been hypothesized that the limiting factor for MSC-based repair processes is the lack of adequate numbers of responsive MSC at the repair site (Caplan, 1994, supra). Thus, it has been suggested that by supplying a sufficient number of MSC to a specific tissue site the repair process can be controlled, since the repair site will supply the appropriate exposure to lineage-specific growth factors and differentiation molecules (Caplan, 1994, supra). Towards this end, several animal studies have demonstrated the feasibility of using autologous MSC for repair of various defects associated with mesenchymal tissue. (For review, see Caplan, et al., in *The Anterior Cruciate Ligament: Current and Future Concepts,* ed. D. W. Jackson, Raven Press, Ltd. NY pp.405–417 (1993). Recent work has demonstrated the feasibility of collection, ex vivo expansion in culture, and intravenous infusion of MSC in humans (Lazarus, et al., *Bone Marrow Transplantation* 16:557–564 (1995); Caplan and Haynesworth, U.S. Pat. No. 5,486,359, hereby incorporated by reference in its entirety). Further, MSC of animal origin have been transfected with retroviruses and have achieved high level gene expression both in vitro and in vivo (Allay, et al., *Blood* 82:477A (1993). Thus, the manipulation of MSC via such techniques seems a promising tool for reconstructive therapies and may be useful for gene therapy.

MSC therapy can serve as a means to deliver high densities of repair-competent cells to a defect site when adequate numbers of MSC and MSC lineage-specific cells are not present in vivo, especially in older and/or diseased patients. In order to efficiently deliver high densities of MSC to a defect site, methods for rapidly producing large numbers of MSC are necessary. MSC have been exposed to a number of growth factors in vitro, but only platelet-derived growth factor (PDGF) showed mitotic activity (Caplan et al., 1994, supra). Methods that increase the ex vivo proliferation rate of MSC will greatly increase the utility of MSC therapy. Similarly, methods that increase in vivo proliferation rate of MSC will enhance the utility of MSC therapy by rapidly increasing local concentrations of MSC at the repair site.

Furthermore, methods that enhance the proliferation rate of lineage-specific descendants of MSC, including but not limited to bone marrow stromal cells, osteoclasts, chondrocytes, and adipocytes, will enhance the therapeutic utility of MSC therapy by increasing the concentration of lineage-specific cell types at appropriate repair sites.

SUMMARY OF THE INVENTION

In one aspect, the present invention provides methods that promote hematopoietic stem and lineage-specific cell proliferation and differentiation, and mesenchymal stem and lineage-specific cell proliferation by contacting the cells with angiotensinogen, angiotensin I (AI), AI analogues, AI fragments and analogues thereof, angiotensin II (AII), AII analogues, AII fragments or analogues thereof or AII $AT_2$ type 2 receptor agonists, either alone or in combination with other growth factors and cytokines.

In another aspect of the present invention, an improved cell culture medium is provided for the proliferation and differentiation of hematopoietic stem and lineage-specific cells, and for the proliferation of mesenchymal stem and lineage-specific cells, wherein the improvement comprises addition to the cell culture medium of an effective amount of angiotensinogen, AI, AI analogues, AI fragments and analogues thereof, AII, AII analogues, AII fragments or analogues thereof or AII $AT_2$ type 2 receptor agonists.

In a further aspect, the present invention provides kits for the propagation of hematopoietic and mesenchymal stem and lineage-specific cells, wherein the kits comprise cell an effective amount of angiotensinogen, AI, AI analogues, AI fragments and analogues thereof, AII, AII analogues, AII fragments or analogues thereof or AII $AT_2$ type 2 receptor agonists, and instructions for using the amount effective of active agent as a cell culture medium supplement. In a preferred embodiment, the kit further comprises a cell culture media. In another preferred embodiment, the kit further comprises a sterile container for cell culturing.

DETAILED DESCRIPTION OF THE PREFERRED EMBODIMENTS

As defined herein, the term "HPC" refers to any hematopoietic pluripotent progenitor cells capable of giving rise to a wide variety of differentiated hematopoietic cell types. Cell types within this definition include, but are not limited to $CD34^+$ bone marrow mononuclear cells (BMMC) (Berardi, et al., *Blood* 86:2123–2129, 1995), PBSC (Fritsch, et al., *Bone Marrow Transplantation* 17:169–178, 1996), cobblestone area forming cells (CAFC) (Lemieux, et al., *Blood* 86:1339–1347, 1995) and 5-FU BM cells (Alcorn and Holyoake, *Blood Reviews* 10:167–176, 1996). As defined herein, the term "HLSC" refers to hematopoietic lineage-specific cells, and includes the progeny of HPC that are committed to a cell-specific differentiation pathway, as well as fully differentiated hematopoietic cells. As defined herein, mesenchymal stem cells (MSC) are pluripotent progenitor cells that possess the ability to differentiate into a variety of mesenchymal tissue, including bone, cartilage, tendon, muscle, marrow stroma, fat and dermis, and include, but are not limited to, cells such as those described in Caplan and Haynesworth, U.S. Pat. No. 5,486,359. As defined herein, "proliferation" encompasses both cell self renewal and cellular proliferation with accompanying differentiation. As defined herein "differentiation" includes both entry into a specific lineage pathway and functional activation of differentiated cells.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (Clouston et al., *Genomics* 2:240–248 (1988); Kageyama et al, *Biochemistry* 23:3603–3609; Ohkubo et al., *Proc. Natl. Acad. Sci.* 80:2196–2200 (1983); each reference hereby incorporated in its entirety). The substance so formed is a decapeptide called angiotensin I (AI) which is converted to AII by the converting enzyme angiotensinase which removes the C-terminal His-Leu residues from AI [SEQ ID NO: 38]. AII is a known pressor agent and is commercially available.

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264:526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990). In addition, AII was shown to be angiogenic in rabbit corneal eye and chick chorioallantoic membrane models (Fernandez, et al., *J. Lab. Clin. Med.* 105:141 (1985); LeNoble, et al., Eur. J. Pharmacol. 195:305–6 (1991). Therefore, AII may accelerate wound repair through increased neovascularization, growth factor release, reepithelialization and/or production of extracellular matrix. However, it is not known in the literature as to whether angiotensinogen, AI, AI analogues, AI fragments and analogues thereof, AII, AII analogues and fragments thereof, or AII receptor agonists would be useful in accelerating the proliferation and differentiation of hematopoietic and mesenchymal stem and lineage-specific cells.

A peptide agonist selective for the AT2 receptor (AII has 100 times higher affinity for AT2 than AT1) has been identified. This peptide is p-aminophenylalanine6-AII ["(p-$NH_2$-Phe)6-AII)"], Asp-Arg-Val-Tyr-Ile-Xaa-Pro-Phe [SEQ ID NO.36] wherein Xaa is p-$NH_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., *BBRC* 187:1083–1090 (1992).

Many studies have focused upon AII(1–7) (AII residues 1–7) or other fragments of AII to evaluate their activity. AII(1–7) elicits some, but not the full range of effects elicited by AII. Pfeilschifter, et al., *Eur. J. Pharmacol.* 225:57–62 (1992); Jaiswal, et al., *Hypertension* 19(Supp. II):II-49-II-55 (1992); Edwards and Stack, *J. Pharmacol.* *Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a., *Br. J. Pharmacol.* 111:652–654 (1994).

As hereinafter defined, a preferred class of AT2 agonists for use in accordance with the present invention comprises AII, AII analogues or active fragments thereof having p-$NH_2$-Phe in a position corresponding to a position 6 of AII. In addition to peptide agents, various nonpeptidic agents (e.g., peptidomimetics) having the requisite AT2 agonist activity are further contemplated for use in accordance with the present invention.

The active AII analogues, fragments of AII and analogues thereof of particular interest in accordance with the present invention comprise a sequence consisting of at least three contiguous amino acids of groups $R^1$–$R^8$ in the sequence of general formula I

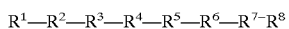

$$R^1-R^2-R^3-R^4-R^5-R^6-R^7-R^8$$

in which $R^1$ and $R^2$ together form a group of formula

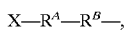

$$X-R^A-R^B-,$$

wherein X is H or a one to three peptide group and a peptide bond between $R^A$ and $R^B$ is labile to aminopeptidase A cleavage;

$R^3$ is selected from the group consisting of Val, Ala, Leu, norLeu, Ile, Gly, Pro, Aib, Acpc and Tyr;

$R^4$ is selected from the group consisting of Tyr, Tyr($PO_3$)$_2$, Thr, Ser, homoSer and azaTyr;

$R^5$ is selected from the group consisting of Ile, Ala, Leu, norLeu, Val and Gly;

$R^6$ is His, Arg or 6-$NH_2$-Phe;

$R^7$ is Pro or Ala; and $R^8$ is selected from the group consisting of Phe, Phe(Br), Ile and Tyr, excluding sequences including $R^4$ as a terminal Tyr group.

Compounds falling within the category of AT2 agonists useful in the practice of the invention include the AII analogues set forth above subject to the restriction that $R^6$ is p-$NH_2$-Phe.

In one class of preferred embodiments, $R^A$ is suitably selected from Asp, Glu, Asn, Acpc (1-aminocyclopentane carboxylic acid), Ala, $Me^2$Gly, Pro, Bet, Glu($NH_2$), Gly, Asp($NH_2$) and Suc. $R^B$ is suitably selected from Arg, Lys, Ala, Orn, Ser(Ac), Sar, D-Arg and D-Lys. Particularly preferred combinations for $R^A$ and $R^B$ are Asp-Arg, Asp-Lys, Glu-Arg and Glu-Lys.

Particularly preferred embodiments of this class include the following: AII, AIII or AII(2–8), Arg-Val-Tyr-Ile-His-Pro-Phe [SEQ ID NO:2]; AII(3–8), also known as des1-AIII or AIV, Val-Tyr-Ile-His-Pro-Phe [SEQ ID NO:3]; AII(1–7), Asp-Arg-Val-Tyr-Ile-His-Pro {SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7]; AII(1–6), Asp-Arg-Val-Tyr-Ile-His [SEQ ID NO:8]; AII(1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6–8), His-Pro-Phe [SEQ ID NO:14] and AII (4–8), Tyr-Ile-His-Pro-Phe [SEQ ID NO:15] were also tested and found not to be effective.

Another class of compounds of particular interest in accordance with the present invention are those of the general formula II

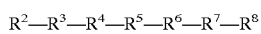

in which $R^2$ is selected from the group consisting of H, Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO$_3$)$_2$, Thr, Ser, homoSer and azaTyr;

$R^5$ is selected from the group consisting of Ile, Ala, Leu, norLeu, Val and Gly;

$R^6$ is His, Arg or 6-NH$_2$-Phe;

$R^7$ is Pro or Ala; and $R^8$ is selected from the group consisting of Phe, Phe(Br), Ile and Tyr.

A particularly preferred subclass of the compounds of general formula II has the formula

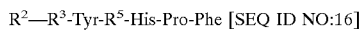

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me$^2$Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr (PO$_3$)$_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra).

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the angiotensinogen, AI, AI analogues, AI fragments and analogues thereof, AII analogues, fragments and analogues of fragments of particular interest in accordance with the present invention, $R^6$ is His, Arg or 6-NH$_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |

TABLE 2-continued

Angiotensin II Analogues

| AII Analogue Name | Amino Acid Sequence | Sequence Identifier |
|---|---|---|
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NQ: 27 |
| Analogue 10 | Asp-Arg-Val-Tyr-Ile-His-Ala-Phe | SEQ ID NO. 28 |
| Analogue 11 | Asp-Arg-Val-Tyr-Ile-His-Ala-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr(Po$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by any conventional method, including, but not limited to, those set forth in J. M. Stewart and J. D. Young, *Solid Phase Peptide Synthesis,* 2nd ed., Pierce Chemical Co., Rockford, Ill. (1984) and J. Meienhofer, *Hormonal Proteins and Peptides, Vol.* 2, Academic Press, New York, (1973) for solid phase synthesis and E. Schroder and K. Lubke, *The Peptides, Vol.* 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Although AII has been shown to increase the proliferation of a number of cell types in vitro, it does not necessarily increase the proliferation of all cell types. Studies have shown that AII accelerates cellular proliferation through the production of transforming growth factor β (TGFβ) (Gibbons et al., *J. Clin. Invest.* 90:456–461 (1992). Thus, since only PDGF is known to be mitogenic for MSC, an ability of AII to effect MSC proliferation would be unexpected. Furthermore, as Emerson (supra) has shown that inclusion of TGF-β in most expansion cultures resulted in a decreased HPC and HLSC yield, it is unexpected that AII, through the action of TGF-β, would be of benefit in such situations. No studies have reported that AII has an effect on the differentiation of either HPC or MSC.

In one aspect of the present invention, a method of increasing in vitro and ex vivo HPC and HLSC proliferation by exposure to angiotensinogen, angiotensin I (AI), AI analogues, AI fragments and analogues thereof, angiotensin II (AII), AII analogues, AII fragments or analogues thereof, or AII AT$_2$ type 2 receptor agonists is disclosed. Experimental conditions for the isolation, purification, ex vivo growth and in vivo mobilization of HPC and HLSC have been reported (Berardi, et al., *Blood* 86(6):2123–2129, 1995; Fritsch, et al., *Bone Marrow Transplantation* 17:169–178, 1996; LaRochelle, et al., *Nature Medicine* 12:1329–1337, 1996; Traycoff, et al., *Experimental Hematology* 24:299–306, 1996; Holyoake, et al., *Blood* 87:4589–4595, 1996; Lemieux, et al., *Blood* 86:1339–1347, 1995; Talmadge, et al., *Bone Marrow Transplantation* 17:101–109, 1996; Bodine, et al., *Blood* 88:89–97, 1996; all references hereby incorporated by reference herein.)

In one embodiment of the invention, HPC are isolated from bone marrow, peripheral blood or umbilical cord blood. HPC is then selected for in these samples. HPC-enriched samples are cultured under appropriate growth conditions, in the presence of angiotensinogen, AI, AI analogues, AI fragments and analogues thereof, AII, AII analogues, AII fragments and analogues thereof and/or AII AT$_2$ type 2 receptor agonists. HPC proliferation is assessed at various time points during culture.

In a preferred embodiment, HPC and HLSC are isolated from bone marrow aspirates from the posterior iliac crest (Caplan and Haynesworth, U.S. Pat. No. 5,486,359). CD34$^+$ HPC are isolated from the aspirate by attaching a biotinylated monoclonal antibody specific for CD34 (available from Becton Dickinson, Sunnyvale, Calif., USA) to a streptavidin affinity column (Ceprate SC; CellPro, Bothell, Wash., USA) and passing the aspirate through the column, followed by appropriate column washing and stripping, according to standard techniques in the art. CD34$^+$ HPC are suspended in culture medium and incubated in the presence of, preferably, between about 0.1 ng/ml and about 1 mg/ml angiotensinogen, AI, AI analogues, AI fragments and analogues thereof, AII, AII analogues, AII fragments and analogues thereof and/or AII AT$_2$ type 2 receptor agonists. The cells are expanded for a period of between 8 and 21 days and cellular proliferation with accompanying differentiation is assessed via phase microscopy following standard methylcellulose colony formation assays (Berardi, et al., supra) at various points during this time period. Similarly, "self-renewal" of HPC is assessed periodically by reactivity to an antibody directed against CD34+.

In a further preferred embodiment, HPC that have been cultured in the presence of angiotensinogen, AI, AI analogues, AI fragments and analogues thereof, AII, AII analogues, AII fragments and analogues thereof and/or AII AT$_2$ type 2 receptor agonists are used for autologous transplantation, to reconstitute a depleted hematopoietic system. Prior to transplantation, the cells are rinsed to remove all traces of culture fluid, resuspended in an appropriate medium and then pelleted and rinsed several times. After the final rinse, the cells are resuspended at between $0.7 \times 10^6$ and $50 \times 10^6$ cells per ml in an appropriate medium and reinfused into a subject through intravenous infusions. Following transplantation, subject peripheral blood samples are evaluated for increases in the number of HPC, HLSC, and more mature blood cells at various time points by standard flow cytometry and cell sorting techniques. (Talmadge, et al., supra).

In another aspect of the present invention, a method of increasing in vitro and ex vivo MSC and lineage-specific mesenchymal cell proliferation by exposure to angiotensinogen, AI, AI analogues, AI fragments and analogues thereof, AII, AII analogues, AII fragments and analogues thereof and/or AII AT$_2$ type 2 receptor agonists is disclosed. Experimental conditions for the isolation, purification and in vitro growth of lineage-specific mesenchymal cells, such as bone-marrow derived stromal cells, have been reported (Johnson and Dorshkind, *Blood* 68(6):1348–1354 (1986); hereby incorporated by reference in its entirety). Other reports describe different conditions for culturing lineage-specific mesenchymal cells in vitro (Bab, et al., *J. Cell Sci.* 84:139–151 (1986); Benayahu, et al., *J. Cellular Physiology* 140:1–7 (1989); both references hereby incorporated by reference in their entirety).

In one embodiment of the present invention, MSC are isolated from bone marrow aspirates from the posterior iliac crest and/or femoral head cancellous bone, purified, resuspended in appropriate growth medium, counted and diluted to an appropriate concentration to seed in tissue culture plates (Caplan and Haynesworth, U.S. Pat. No. 5,486,359). Purified MSC are cultured in an appropriate growth medium and growth conditions in a humidified atmosphere. The cells are allowed sufficient time to attach to the tissue culture dish, whereupon non-attached cells are discarded. Adherent cells are placed in growth medium at 37° C. in a humidified atmosphere in the presence of, preferably, between about 0.1 ng/ml and about 1 mg/ml angiotensinogen, AI, AI analogues, AI fragments and analogues thereof, AII, AII analogues, AII fragments and analogues thereof and/or AII AT$_2$ type 2 receptor agonists. The cells are expanded for a period of between 2 and 21 days and cellular proliferation is assessed at various time points during this time period. Subsequent medium changes are performed as needed. When the primary cultures are nearly confluent, the cells are harvested for reinfusion into a subject. Cells are examined microscopically to verify the absence of contamination. The cells are rinsed to remove all traces of culture fluid, resuspended in an appropriate medium and then pelleted and rinsed several times. After the final rinse, the cells are resuspended at between $0.7 \times 10^6$ and $50 \times 10^6$ cells per ml in an appropriate medium and reinfused into a subject through intravenous infusions. Subjects are evaluated for MSC proliferation in vivo by means of a repeat diagnostic bone marrow aspirate and biopsy to be compared with the original aspirate and biopsy. In a preferred embodiment, in vivo proliferation is assessed by reactivity to an antibody directed against a protein known to be present in higher concentrations in proliferating cells than in non-proliferating cells, such as proliferating cell nuclear antigen (PCNA, or cyclin). Such antibodies are commercially available from a number of sources, including Zymed Laboratories (South San Francisco, Calif., USA).

In a preferred embodiment, isolated MSC are placed into Dulbecco's medium MEM (DMEM-LG) (Gibco, Grand Island, N.Y., USA). The cells are purified by a series of steps. Initially, the cells are pelleted and resuspended in Complete Medium. The cells are centrifuged through a 70% Percoll (Sigma Corporation, St. Louis, Mo., USA) gradient at 460×g for 15 minutes, the top 25% of the gradients are transferred to a tube containing 30 ml of Complete Medium and centrifuged to pellet the cells, which will then be resuspended in Complete Medium, counted and diluted to seed in 100-mm plates at $50 \times 10^6$ nucleated cells per plate.

In a further preferred embodiment, purified MSC are cultured in Complete Medium at 37° C. in a humidified atmosphere containing 95% air and 5% $CO_2$ and the cells are allowed to attach for 3 days, whereupon non-adherent cells are removed by changing the culture medium. Cellular proliferation of adherent cells and the presence of normal MSC morpholgy are assessed by phase microscopy at various time points during the subsequent growth period. Subsequent medium changes are performed every four days. When the primary cultures are nearly confluent, the cells are detached with 0.25% trypsin containing 0.1 mM EDTA (Gibco) and either diluted and replated as second passage cells, or used for reinfusion into a subject. Preferably, cells are rinsed free of culture fluid using Tyrode's solution (Gibco). After the final rinse, cells are placed in Tyrode's solution and placed in an incubator at 37° C. for one hour in order to shed serum proteins. The Tyrode's solution is removed and the cells are preferably placed into TC199 medium (Gibco) supplemented with 1% serum albumin. The cells are rinsed a number of times with this medium and after the final rinse MSC are resuspended in TC199 plus 1% serum albumin. Subsequently, MSC are injected slowly intravenously over 15 minutes. Evaluation of subsequent bone marrow aspirates are conducted up to 8 weeks after injection.

In a preferred embodiment, assessment of the in vivo proliferative effect of angiotensinogen, AI, AI analogues, AI fragments and analogues thereof, AII, AII analogues, AII fragments and analogues thereof and/or AII AT$_2$ type 2 receptor agonists on MSC and mesenchymal lineage-specific cells is done by histochemical evaluations of various tissues. In a preferred embodiment, in vivo proliferation of MSC and mesenchymal lineage-specific cells is assessed by reactivity to an antibody directed against a protein known to be present in higher concentrations in proliferating cells than in non-proliferating cells, such as proliferating cell nuclear antigen (PCNA, or cyclin; Zymed Laboratories).

In a further aspect of the present invention, the effect of angiotensinogen, AI, AI analogues, AI fragments and analogues thereof, AII, AII analogues, AII fragments and analogues thereof and/or AII AT$_2$ type 2 receptor agonists on HPC, HLSC differentiation are assessed by examination of changes in gene expression, phenotype, morphology, or any other method that distinguishes a cell undergoing differentiation from a lineage-specific cell. In a preferred embodiment, macrophage differentiation to an elicited or activated state is assessed after exposure to angiotensinogen, AI, AI analogues, AI fragments and analogues thereof, AII, AII analogues, AII fragments and analogues thereof and/or AII AT$_2$ type 2 receptor agonists, as described above. The macrophages are assessed for phagocytotic ability by any of the well known art methods, including but not limited to determination of the number of macrophages that have ingested opsonized yeast particles, and the number of yeast per macrophage ingested. (Rodgers and Xiong, *Fundamental and Applied Toxicology* 33:100–108 (1996)).

In another preferred embodiment, the respiratory burst activity of leukocytes is assessed after exposure to angiotensinogen, AI, AI analogues, AI fragments and analogues thereof, AII, AII analogues, AII fragments and analogues thereof and/or AII $AT_2$ type 2 receptor agonists as described above. The leukocytes are assessed for respiratory burst activity by any method known in the art including, but not limited to, the ability to generate hydrogen peroxide via the respiratory burst system. (Rodgers et al., *International Journal of Immunopharmacology* 10:111–120 (1988); Rodgers, In: *Modern Methods in Immunotoxicology* (ed. G. Burleson), Wiley Liss 2:67–77 (1995)).

Macrophage activation by the compounds of the present invention can be utilized for treating viral and microbial infections, stimulating macrophages to produce cytokines made by activated macrophages, improving macrophage presentation to T cells, and augmenting anti-tumor immunity in a mammal.

In another aspect of the present invention angiotensinogen, AI, AI analogues, AI fragments and analogues thereof, AII, AII analogues, AII fragments and analogues thereof and/or AII $AT_2$ type 2 receptor agonists are used to increase in vivo HPC, HLSC, MSC and mesenchymal lineage-specific cell proliferation. For use in increasing proliferation of HPC, HLSCP, MSC and mesenchymal lineage-specific cells, angiotensinogen, AI, AI analogues, AI fragments and analogues thereof, AII, AII analogues, AII fragments and analogues thereof and/or AII $AT_2$ type 2 receptor agonists may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrastemal, intratendinous, intraspinal, intracranial, intrathoracic, infusion techniques or intraperitoneally.

In a further embodiment of the present invention, a method of increasing in vivo HPC, HLSC, MSC and lineage-specific mesenchymal cell proliferation by exposure to angiotensinogen, AI, AI analogues, AI fragments and analogues thereof, AII, AII analogues, AII fragments and analogues thereof and/or AII $AT_2$ type 2 receptor agonists is disclosed, either in the presence or absence of other growth factors and cytokines. Examples of such growth factors and cytokines include, but are not limited to lympholines, interleukins—1, 2, 3, 4, 5, 6, 7, 8, 9, 10, 11, granulocyte colony-stimulating factor, granulocyte/macrophage colony stimulating factor, macrophage colony-stimulating factor, tumor necrosis factor, epidermal growth factor, fibroblast growth factor, platelet derived growth factor, transforming growth factor beta, and stem cell factor.

The angiotensinogen, AI, AI analogues, AI fragments and analogues thereof, AII, AII analogues, AII fragments and analogues thereof and/or AII $AT_2$ type 2 receptor agonists may be made up in a solid form (including granules, powders or suppositories) or in a liquid form (e.g., solutions, suspensions, or emulsions). The compounds of the invention may be applied in a variety of solutions. Suitable solutions for use in accordance with the invention are sterile, dissolve sufficient amounts of the peptide, and are not harmful for the proposed application. In this regard, the compounds of the present invention are very stable but are hydrolyzed by strong acids and bases. The compounds of the present invention are soluble in organic solvents and in aqueous solutions at pH 5–8.

The angiotensinogen, AI, AI analogues, AI fragments and analogues thereof, AII, AII analogues, AII fragments and analogues thereof and/or AII $AT_2$ type 2 receptor agonists may be subjected to conventional pharmaceutical operations such as sterilization and/or may contain conventional adjuvants, such as preservatives, stabilizers, wetting agents, emulsifiers, buffers etc.

While angiotensinogen, AI, AI analogues, AI fragments and analogues thereof, AII, AII analogues, AII fragments and analogues thereof and/or AII $AT_2$ type 2 receptor agonists can be administered as the sole active pharmaceutical agent, they can also be used in combination with one or more other agents. When administered as a combination, the therapeutic agents can be formulated as separate compositions that are given at the same time or different times, or the therapeutic agents can be given as a single composition.

For administration, the angiotensinogen, AI, AI analogues, AI fragments and analogues thereof, AII, AII analogues, AII fragments and analogues thereof and/or AII $AT_2$ type 2 receptor agonists are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Formulations suitable for topical administration include liquid or semi-liquid preparations suitable for penetration through the skin (e.g., liniments, lotions, ointments, creams, or pastes) and drops suitable for administration to the eye, ear, or nose.

The dosage regimen for increasing in vivo proliferation or differentiation of HPC, HLSCP, MSC and lineage-specific mesenchymal cell with angiotensinogen, AI, AI analogues, AI fragments and analogues thereof, AII, AII analogues, AII fragments and analogues thereof and/or AII $AT_2$ type 2 receptor agonists is based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods. Dosage levels of the order of between 0.1 ng/kg and 1 mg/kg angiotensinogen, AI, AI analogues, AI fragments and analogues thereof, AII, AII analogues, AII fragments and analogues thereof and/or AII $AT_2$ type 2 receptor agonists per body weight are useful for all methods of use disclosed herein.

The treatment regime will vary depending on the disease being treated, based on a variety of factors, including the type of injury, the age, weight, sex, medical condition of the individual, the severity of the condition, the route of administration, and the particular compound employed. For example, angiotensinogen, AI, AI analogues, AI fragments and analogues thereof, AII, AII analogues, AII fragments and analogues thereof and/or AII $AT_2$ type 2 receptor agonists are administered to an oncology patient for up to 30 days prior to a course of radiation therapy. The therapy is administered for 1 to 6 times per day at dosages as described above. In another example, in order to mobilize hematopoietic lineage-specific cells for donation by plasmapheresis the therapy is for up to 30 days for 1 to 6 times per day.

In a preferred embodiment of the present invention, the angiotensinogen, AI, AI analogues, AI fragments and analogues thereof, AII, AII analogues, AII fragments and analogues thereof and/or AII $AT_2$ type 2 receptor agonist is administered topically. A suitable topical dose of active ingredient of angiotensinogen, AI, AI analogues, AI fragments and analogues thereof, AII, AII analogues, AII fragments and analogues thereof and/or AII $AT_2$ type 2 receptor agonists is preferably between about 0.1 ng/ml and about 1 mg/ml administered twice daily. For topical administration, the active ingredient may comprise from 0.0001% to 10% w/w, e.g., from 1% to 2% by weight of the formulation, although it may comprise as much as 10% w/w, but preferably not more than 5% w/w, and more preferably from 0.1% to 1% of the formulation.

In another aspect of the present invention, an improved cell culture medium is provided for the proliferation and differentiation of hematopoietic and mesenchymal stem and lineage-specific cells, wherein the improvement comprises addition to the cell culture medium of an effective amount of angiotensinogen, AI, AI analogues, AI fragments and analogues thereof, AII, AII analogues, AII fragments and analogues thereof and/or AII $AT_2$ type 2 receptor agonists, as described above. Any cell culture media that can support the growth of hematopoietic and mesenchymal stem and lineage-specific cells can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, OPTI-MEM® Reduced-Serum Medium, RPMI Medium, and Macrophage-SFM Medium or combinations thereof.

The improved cell culture medium can be supplied in either a concentrated (ie: 10x) or non-concentrated form, and may be supplied as either a liquid, a powder, or a lyophilizate. The cell culture may be either chemically defined, or may contain a serum supplement. Culture media is commercially available from many sources, such as GIBCO BRL (Gaithersburg, Md.) and Sigma (St. Louis, Mo.)

In a further aspect, the present invention provides kits for the propagation of hematopoietic and mesenchymal stem and lineage-specific cells, wherein the kits comprise an effective amount of angiotensinogen, AI, AI analogues, AI fragments and analogues thereof, AII, AII analogues, AII fragments and analogues thereof and/or AII $AT_2$ type 2 receptor agonists, and instructions for its use as a cell culture media supplement.

In a preferred embodiment, the kits further comprise cell culture growth medium. Any cell culture media that can support the growth of hematopoietic and mesenchymal stem and lineage-specific cells can be used with the present invention. Examples of such cell culture media are described above. The cell culture medium can be supplied in either a concentrated (ie: 10x) or non-concentrated form, and may be supplied as either a liquid, a powder, or a lyophilizate. The cell culture may be either chemically defined, or may contain a serum supplement.

In a further preferred embodiment, the kit further comprises a sterile container, which can comprise either a sealed container, such as a cell culture flask, a roller bottle, or a centrifuge tube, or a non-sealed container, such as a cell culture plate or microtiter plate (Nunc; Naperville, Ill.).

In another preferred embodiment, the kit further comprises an antibiotic supplement for inclusion in the reconstituted cell growth medium. Examples of appropriate antibiotic supplements include, but are not limited to actinomycin D, FUNGIZONE®, kanamycin, neomycin, nystatin, penicillin, streptomycin, or combinations thereof (GIBCO).

The present invention, by providing a method for enhanced proliferation of HPC and HLSC, will greatly increase the clinical benefits of HPC transplantation. This is true both for increased "self-renewal", which will provide a larger supply of HPC capable of reconstituting the entire hematopoietic system, and for proliferation with differentiation, which will provide a larger supply of lineage-specific cells, for more rapid reconstitution of mature, functioning blood cells. Similarly, methods that increase in vivo proliferation of HPC will enhance the utility of HPC transplantation therapy by rapidly increasing local concentrations of HPC (and HLSC) in the bone marrow, and thereby more rapidly producing functioning blood cells.

Similarly, methods that increase the proliferation of MSC and mesenchymal lineage-specific cells, will greatly increase the utility of MSC therapy in the repair of skeletal tissues such as bone, cartilage, tendon and ligament. More rapid proliferation of large numbers of MSC and mesenchymal lineage-specific cells will permit more efficient delivery of high densities of these cells to a defect site and more rapid in vivo amplification in the local concentration of stem and lineage-specific cells at an appropriate repair site.

The method of the present invention also increases the potential utility of HPC and HLSC as vehicles for gene therapy in hematopoietic disorders, as well as MSC and mesenchymal lineage-specific cells as vehicles for gene therapy in skeletal disorders by more efficiently providing a large number of such cells for transfection, and also by providing a more efficient means to rapidly expand transfected HPC, HLSC, MSC and mesenchymal lineage-specific cells.

The present invention may be better understood with reference to the accompanying examples that are intended for purposes of illustration only and should not be construed to limit the scope of the invention, as defined by the claims appended hereto.

EXAMPLE 1

Macrophage Differentiation: Phagocytosis

Resident peritoneal macrophages have very little phagocytic activity. Exposure of macrophages to inflammatory or activating agents will increase this macrophage function. Resident peritoneal macrophages were harvested from C57B1/6 mice or Sprague Dawley rats and resuspended at a concentration of $1 \times 10^6$ cells/ml in phosphate buffered saline (PBS). Five separate 0.5 ml cell aliquots were placed on a glass coverslip in a 35 mm petri dish. Prior to incubation, either 0.5 ml of PBS, AII, or AII analogues or fragments at between 1–1000 ug/ml final concentration was added to the individual cover slips. The dishes containing the cover slips were then incubated at 37° C. for 4 hours, after which the cover slips were washed 3 to 6 times with PBS. Opsonized yeast particles (Sigma Chemical Co.) (yeast opsonized with adult serum from the same species as that under study) were added to the cover slips and incubated for 2 hours, after which the cover slips were again washed with PBS and inverted onto a glass slide. The number of macrophages that ingested yeast and the number of yeast per macrophage ingested was then determined microscopically. At least 100 macrophages per coverslip were counted. The data from this study are summarized in Tables 3 and 4 and FIGS. 1 and 2. Table 5 describes the AII analogues and fragments used in these studies.

Exposure to 10 μg/ml or greater AII tremendously increased the phagocytic capability of peritoneal macrophages. Less than 1% of cells were phagocytic in the resident population (0.01 yeast per cell observed). After exposure to AII this increased to over 25% phagocytic at the highest concentration with on average 1 yeast observed per macrophage (25 fold increase in the number of macrophages able to phagocytose and a 100-fold increase in the number of particles phagocytized).

As shown in Table 4, both concentration of the peptides tested (with the exception of GSD 28) elevated that phagocytic capability of rat macrophages. However, none of the analogues resulted in the magnitude of an effect observed with AII. This suggests that AII and, to a lesser extent, AII analogues will stimulate macrophage differentiation to an elicited or activated state, which leads to the ingestion and clearance of bacteria and cellular debris.

TABLE 3

Effect of AII on the Phagocytic Capability of Murine Peritoneal Macrophages

| | Concentration of AII (μg/ml) | | | | |
|---|---|---|---|---|---|
| | 0 | 1 | 10 | 100 | 1000 |
| Yeast # | # Macrophages with Yeast | | | | |
| 0 | 100 | 100 | 100 | 100 | 100 |
| 1–3 | 1 | 1 | 3 | 10 | 20 |
| 4–6 | 0 | 0 | 4 | 10 | 20 |
| 7–9 | 0 | 0 | 0 | 0 | 0 |
| % Ingesting | 1 | 1 | 6.5 | 16.7 | 25.6 |
| # Yeast/MO | 000.01 | 0.01 | 0.24 | 0.58 | 1.00 |

TABLE 4

Effect of AII on the Phagocytic Capability of Rat Peritoneal Macrophages

| (Peptide) | Number of Macrophages with Yeast (Yeast Number) | | | | | |
|---|---|---|---|---|---|---|
| μg/ml | 0 | 1–3 | 4–6 | ≧7 | % w/Yeast | #/Cell |
| AII-0 | 88 | 2 | 0 | 0 | 2.2 | 0.04 |
| 100 | 90 | 30 | 20 | 0 | 35.7 | 1.14 |
| 1000 | 50 | 54 | 40 | 25 | 70.4 | 2.86 |
| AII(1–7)-0 | 90 | 3 | 0 | 0 | 3.2 | 0.06 |
| 100 | 100 | 21 | 5 | 0 | 20.6 | 0.53 |
| 1000 | 90 | 30 | 10 | 0 | 30.8 | 0.85 |
| GSD22A-0 | 90 | 1 | 0 | 0 | 1.1 | 0.02 |
| 100 | 100 | 26 | 5 | 0 | 23.7 | 0.59 |
| 1000 | 100 | 22 | 1 | 0 | 18.7 | 0.40 |
| GSD 24-B-0 | 100 | 2 | 0 | 0 | 2.0 | 0.04 |
| 100 | 100 | 25 | 5 | 0 | 23.1 | 0.58 |
| 1000 | 100 | 10 | 0 | 0 | 9.1 | 0.18 |
| GSD28-0 | 100 | 1 | 0 | 0 | 1.0 | 0.02 |
| 100 | 100 | 1 | 0 | 0 | 1.0 | 0.02 |
| 1000 | 100 | 1 | 0 | 0 | 1.0 | 0.02 |

TABLE 5

Designation for Analogues

| Name | Abbreviation | Sequence | SEQ ID NO: |
|---|---|---|---|
| GSD 28 | Ile$^8$-AII | DRVYIHPI | SEQ ID NO:38 |
| GSD 24B | Pro$^3$-AII | DRPYIHPF | SEQ ID NO:35 |
| GSD 22A | Ala$^4$-AII | RVYAHPF | SEQ ID NO:18 |
| AII(1–7) | | DRVYIHP | SEQ ID NO:4 |

EXAMPLE 2

Leukocyte Differentiation: Respiratory Burst

The respiratory burst of leukocytes (macrophages and polymorphonuclear neutrophils) is one component of the mediator system used to kill bacteria. As with phagocytosis, the level of this respiratory burst activity in resident macrophages is low. With differentiation, either to an elicited (inflammatory) or activated state, this functional activity is significantly elevated. Studies were conducted to assess the effect of in vitro exposure of murine or rat peritoneal macrophages and human peripheral blood mononuclear cells (PBMC) to various concentrations of AII on the capacity to generate hydrogen peroxide via the respiratory burst system. For the human studies, five different donors were examined.

The murine or rat peritoneal cells were harvested by lavage with 5–15 ml of cold PBS with 0.5% bovine serum albumin. The human PBMC were harvested by venipuncture from normal human volunteers and isolated from peripheral blood by FICOLL HYPAQUE® density centrifugation. After isolation, the cells were resuspended at 1×10$^6$ cells/ml and placed at 100 μl per well into 96 well plates. The cells were incubated with various concentrations of AII or AII analogues for 4 hours at 37° C. The cells were then pre-loaded with a fluorescent probe for hydrogen peroxide, 2,7 dichlorofluorescein acetate, which is nonfluorescent in the absence of hydrogen peroxide. Fifteen minutes later, 10 ng/ml of phorbol myristate acetate (+PMA) or PBS (−PMA) was added to stimulate the production of hydrogen peroxide. One hour after stimulation the level of fluorescence produced was measured on a Cytofluor 2350 multiwell fluorometer. Representative results from this study are shown in FIGS. 3–4.

In the absence of PMA or peptide, no hydrogen peroxide production is observed. Some variability in the response to AII was seen (i.e. the concentration of AII necessary to increase the level of this function); however, in all studies AII increased the ability of leukocytes to generate hydrogen peroxide both alone and in response to stimulation with PMA. Further, the effect of pre-exposure to analogues of AII (GSD 22A, GSD 24B, GSD 28 and AII(1–7)) on the respiratory burst activity of PBMC was assessed (FIGS. 5–8). For all analogues, a much higher concentration of the peptide was needed to increase the respiratory burst activity. Up to 100 times more of these analogues were necessary; however, an increase in the respiratory burst capacity was observed for all analogues tested. The analogues were able to stimulate that function both in the presence and absence of PMA. These data indicate that AII was able to stimulate the differentiation of monocytes/macrophages from three species.

EXAMPLE 3

Proliferative Response of Human Lymphocytes

Upon stimulation of lymphocytes with mitogen or antigen, these cells undergo blastogenesis and proliferation. In the absence of such stimuli, proliferation is seldom observed. One method to measure cellular proliferation in a short term assay is via measurement of the amount of the nucleotide thymidine that is incorporated into newly synthesized DNA. The effect of AII on the proliferation of human PBMC in the presence and absence of pokeweed mitogen ("PWM") was assessed.

Human PBMC were collected from normal volunteers and isolated via FICOLL HYPAQUE® (Sigma Chemical, St. Louis) density centrifugation. After isolation of the buffy coat, the cells were washed 3× to remove the FICOLL HYPAQUE, counted in trypan blue (0.01%) and resuspended at a concentration of $1\times10^6$ cells/ml in RPMI 1640 containing 10% fetal calf serum and antibiotics. A 100 µl aliquot of cells was added to each well. Thereafter, various concentrations (0.1 to 1000 µg/ml final concentration) of AII in RPMI 1640 containing 10% FCS and antibiotics were added to various wells in triplicate. To the appropriate wells, PWM (20 µg/ml final concentration) was added. These plates were incubated at 37° C. in 5% $CO_2$ for 48 hours. Subsequently, 0.5 µCi of $^3$H-thymidine was added to each well, which were incubated at 37° C. for an additional 24 hours prior to harvest by a multiwell automated sample harvester (Skatron) onto glass fiber filters. These filters were dried, placed in scintillation fluid and the amount of thymidine incorporated was determined by beta counting. The results are shown in FIG. 9 and Table 6.

In the absence of mitogen, no increase in thymidine incorporation was observed after exposure to AII. However, in two separate experiments (cells from 2 different donors) AII was shown to increase the amount of thymidine incorporated in response to PWM. These data show that AII is able to increase the proliferation of cells from the hematopoietic lineage (e.g. lymphocytes).

TABLE 6

Effect of AII on the Proliferation of Human PBMC

| AII Concentration | Proliferation Index cpm $^3$H-Thymidine Incorporated (SI[a]) | |
| --- | --- | --- |
| | Experiment 1[b] | Experiment 2 |
| 0 | 1146.3 (3.63) | 2022.0 (31.11) |
| 0.1 | 1329.0 (3.54) | 2135.0 (38.13) |
| 1 | 1411.2 (5.88) | 2996.0 (62.42) |
| 10 | 1427.0 (5.34) | 3946.0 (75.88) |
| 100 | 1552.1 (11.41) | 3747.0 (69.39) |
| 1000 | 1551.5 (15.48) | 4302.0 (89.63) |

[a]SI = Stimulation Index is calculated from the ration of the counts incorporated into stimulated cultures divided by counts in cultures without mitogen (FCS only-basal proliferation). This is shown in the parentheses.
[b]The effect of AII on the proliferation of PBMC from two separate donors are shown in this table.

EXAMPLE 4
Rat Mesenchymal Stem Cell Proliferation

These studies were conducted to determine the effect that AII would have on the proliferation of MSC. Bone marrow cells were harvested from the femur and tibia of female Sprague Dawley rats by flushing the bones with Dulbecco's Minimal Essential Medium-High Glucose ("DMEM-HG") with a syringe and an 18 gauge needle. These cells were cultured in 24 well plates at $5\times10^3$ cells/mm$^2$ in DMEM-HG containing selected lots of fetal calf serum (FCS) and antibiotics (complete medium) at 37° C. incubator containing 5% $CO_2$ in air. Twenty-four hours after the initiation of the cultures the medium and nonadherent cells were aspirated and fresh medium was added. To each of these several wells, complete medium with (1 to 100 µg/ml) or without AII was added. The migration of cells from the clones and their proliferation was followed by microscopic examination. Every 4 days the old medium was removed and fresh medium was added to the cultures.

The data from these experiments are shown in FIGS. 10 and 11. Addition of AII to the cultures significantly increased the number of sites from which the MSC were migrating (CFU) and the size (number of cells) of the colonies formed. This occurred only in the presence of serum that in itself would support MSC growth, albeit to a lesser extent. As can be seen, AII caused an increase in the number of MSC in a concentration dependent manner at all time points examined in the presence of two different serum lots. These data support the hypothesis that AII can increase the proliferation of rat MSC.

EXAMPLE 5
Effect of Angiotensin II on Murine Lineage-specific Cells

HPC were harvested from C57Bl/6 mice by immunomagnetic affinity chromatography and placed in semi-solid cultures with optimal growth medium. At various times after initiation of culture, the formation of colonies and the size of the colonies (number of cells/colony) was assessed microscopically.

Female C57Bl/6 mice were purchased from Simonson and used as a source of bone marrow cells in this study. The bone marrow was harvested, either from untreated mice or from mice injected with 5-fluorouracil (5-FU) (3 mg/mouse; approximately 150 mg/kg) in the tail vein 48 hours before harvest, from the femur and tibia of mice by flushing with phosphate buffered saline (PBS), pH 7.4, containing 2% fetal bovine serum (FBS) with a 21-gauge needle. The eluant from the flushing was centrifuged and the pellet was resuspended at $4\times10^7$ nucleated cells/ml in PBS containing PBS containing 2% FBS and 5% normal rat serum.

The reagents for immunomagnetic labeling were purchased from Stem Cell Technologies, Inc. (Vancouver, BC). Biotin-labeled monoclonal antibodies to the following murine lineage-specific cell surface antigens were included in a cocktail for HPC enrichment and used according to the manufacturer's instructions: CD5 (Ly-1), CD45-R (B220), CD11b (Mac-1), Myeloid Differentiation Antigen (Gr-1) and Erythroid Cells (TER 119). Ten µl of antibody cocktail was added for each of the 2 sets of bone marrow (normal and 5-FU-treated), mixed and allowed to incubate at 4° C. for 15 minutes. The cells were then resuspended at $4\times10^7$ cells/ml in PBS containing 2% FBS. The antibody cocktail was then washed out and 100 µl anti-biotin tetramer was added for each ml of cells. The suspension was mixed and incubated at 4° C. for 15 minutes. Sixty µl of magnetic colloid was then added for each ml of cells, the combination was mixed and incubated at 4° C. for 15 minutes to yield the immunomagnetically-labeled bone marrow cells.

A column containing a stainless steel matrix was prepared by washing the matrix with PBS followed by washing with PBS containing 2% protein. The immunomagnetically-labeled bone marrow cells were loaded onto the column and unlabeled cell-containing medium (enriched HPC) was collected in the flow through fraction at a flow rate of 0.2 ml/minute. Medium was added to the top of the column so that it did not run dry until 8 to 10 ml of enriched HPC were harvested. Approximately 2% of the cells loaded onto the column were isolated in the enriched HPC fractions.

The enriched HPC cell fractions were diluted into a semi-solid medium containing 0.9% methylcellulose in alpha minimal essential medium (alpha MEM), 30% fetal calf serum, 1% bovine serum albumin, $10^{-4}$ M 2-mercaptoethanol, 2 mM L-glutamine, and 2% conditioned medium containing colony stimulating factors. The conditioned medium was supernatant from splenocyte cultures ($1\times10^6$ cells/ml) incubated for 48 hours in RPMI 1640 containing 10 µg/ml pokeweed mitogen (PWM), 10% FCS, and antibiotics. Various concentrations of AII, between 0 and 100 µg/ml were added in a small volume to the wells of microtiter dishes, to which between $2\times10^4$ cells/ml for the normal and $2.5\times10^4$ cells/ml for the 5-FU treated cells. The cells were incubated at 37° C. and 5% $CO_2$ for 14 days. At day 14 only, macroscopic cell colonies were observed in the wells containing enriched HPC from untreated (normal)

mice treated with 10 μg/ml (18 macroscopic colonies) and 100 μg/ml AII (10 macroscopic colonies). Microscopic evaluation of the cells was performed at various days after initiation of incubation, and the results are summarized in FIGS. 12–17.

FIGS. 12–14 and 16 represent the number of colonies containing more than a certain number of cells/colony as a function of the duration and concentration of AII exposure (FIGS. 12–14 for normal cells; FIG. 16 for 5-FU treated cells.) FIGS. 15 and 17 represents the number of cells per colony seen after incubation of bone marrow from normal or 5-FU treated mice with various concentrations of AII as a function of time. The results clearly demonstrate that HPC colony size increases proportionately with exposure to increased concentrations of AII, and thus that AII increases HPC proliferation.

EXAMPLE 6
Effect of AII Analogues and Fragments on Rat Mesenchymal Stem Cell Proliferation These studies were conducted to determine the effect that inclusion of AII analogues and fragments in the cell culture of MSC would have on the proliferation of these cells. Bone marrow cells were harvested from the femur and tibia of female Sprague Dawley rats by flushing the bones with Dulbecco's Minimal Essential Medium-High Glucose ("DMEM-HG") with a syringe and an 18 gauge needle. These cells were cultured in 24 well plates at $5 \times 10^3$ cells/mm$^2$ in DMEM-HG containing selected lots of fetal calf serum (FCS) and antibiotics (complete medium) at 37° C. incubator containing 5% $CO_2$ in air. Twenty-four hours after the initiation of the cultures the medium and nonadherent cells were aspirated and fresh medium was added. To each of these several wells, complete medium with (1 to 100 μg/ml) or without AII analogues and fragments (see Table 5) was added. The migration of cells from the clones and their proliferation was followed by microscopic examination. Every 4 days the old medium was removed and fresh medium was added to the cultures.

Addition of AII analogues or AII fragments to these cultures had a profound effect on the number of sites from which MSC were migrating (CFU) and the size (number of cells) of the colonies formed. The results from these studies can be seen in FIGS. 18–21. As can be seen, AII analogues and fragments caused an increase in the number of MSC at all time points examined. These data indicate that AII analogues and fragments can increase the proliferation of rat MSC.

EXAMPLE 7
Proliferation of MSC Lineage-Specific Cells in the Presence of AII

Mesenchymal stem cells isolated from bone marrow and grown under appropriate conditions can express characteristics of multiple cell types, including cells involved in the generation of bone, cartilage, muscle and tendons. Osteogenic cells (cells that can form bone tissue) express the enzyme alkaline phosphatase when cultured in medium that drives them toward their osteogenic differentiation.

Figure 22:
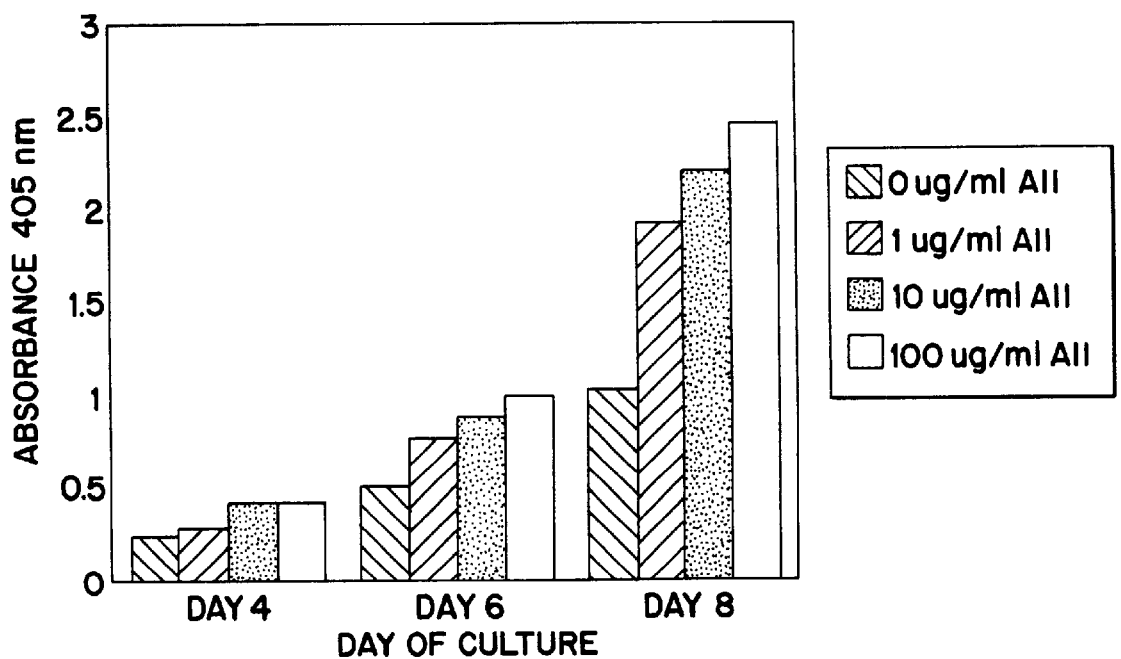
Figure 23:
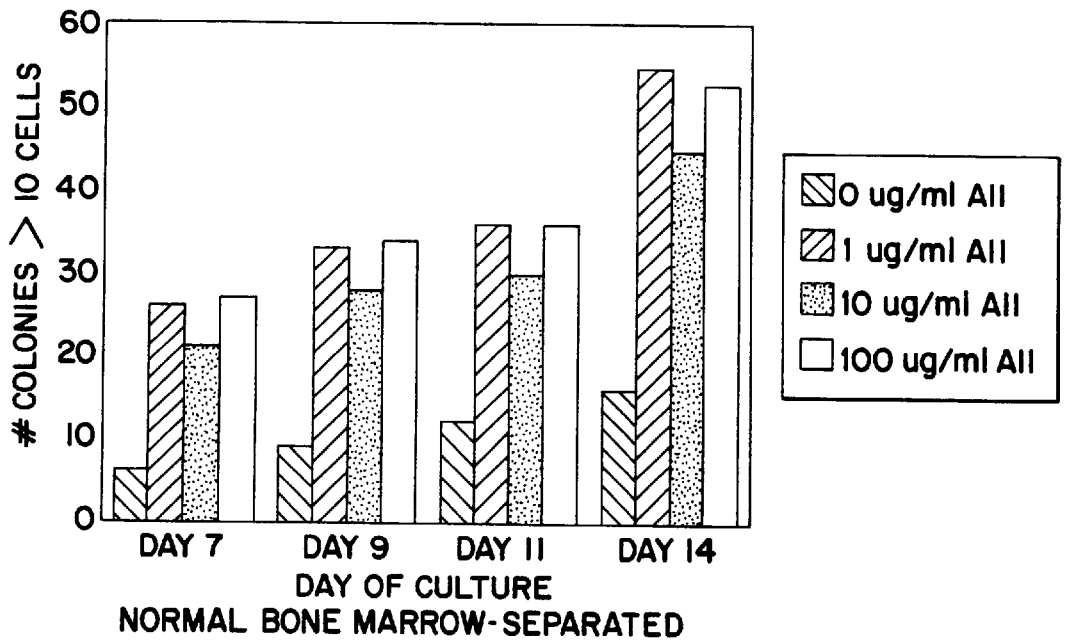
Figure 24:
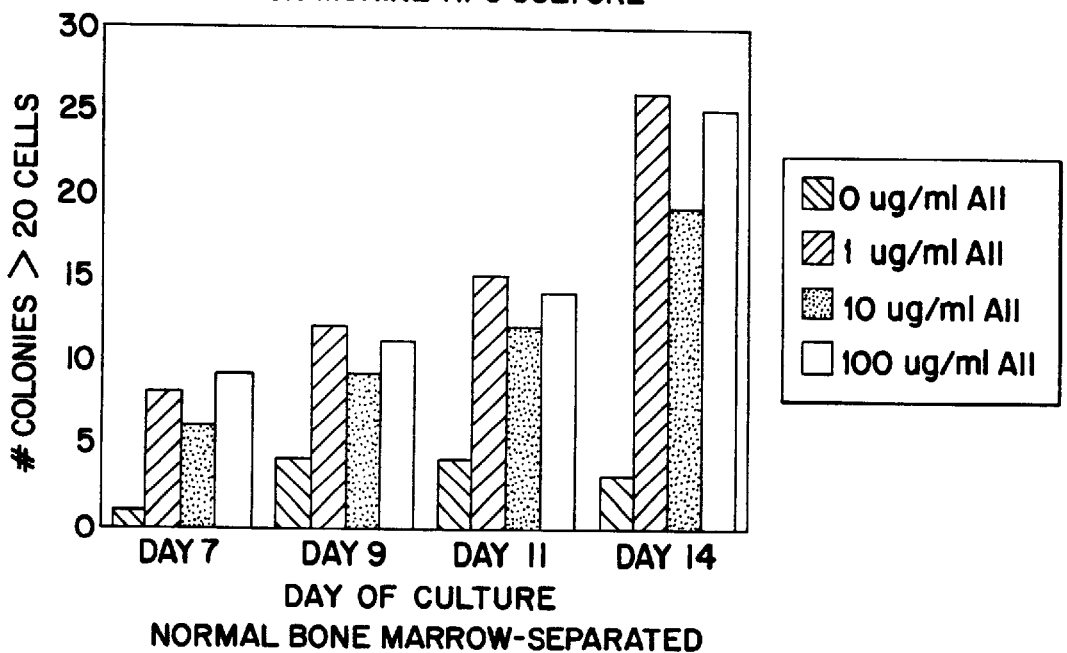
Figure 25:
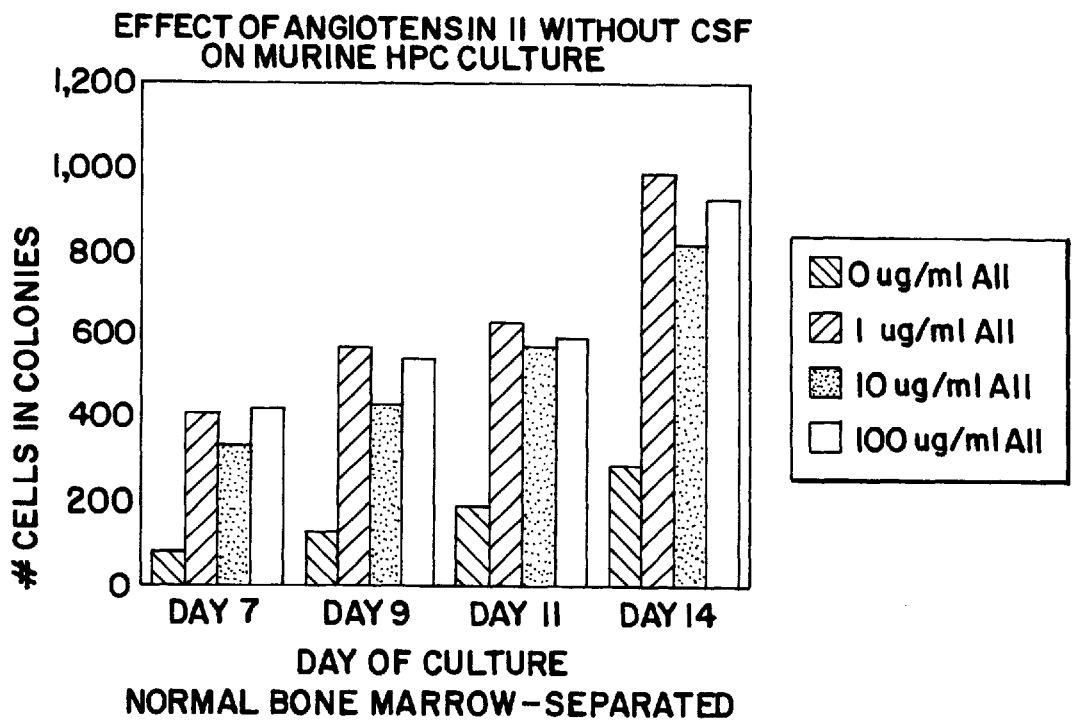
Figure 26:
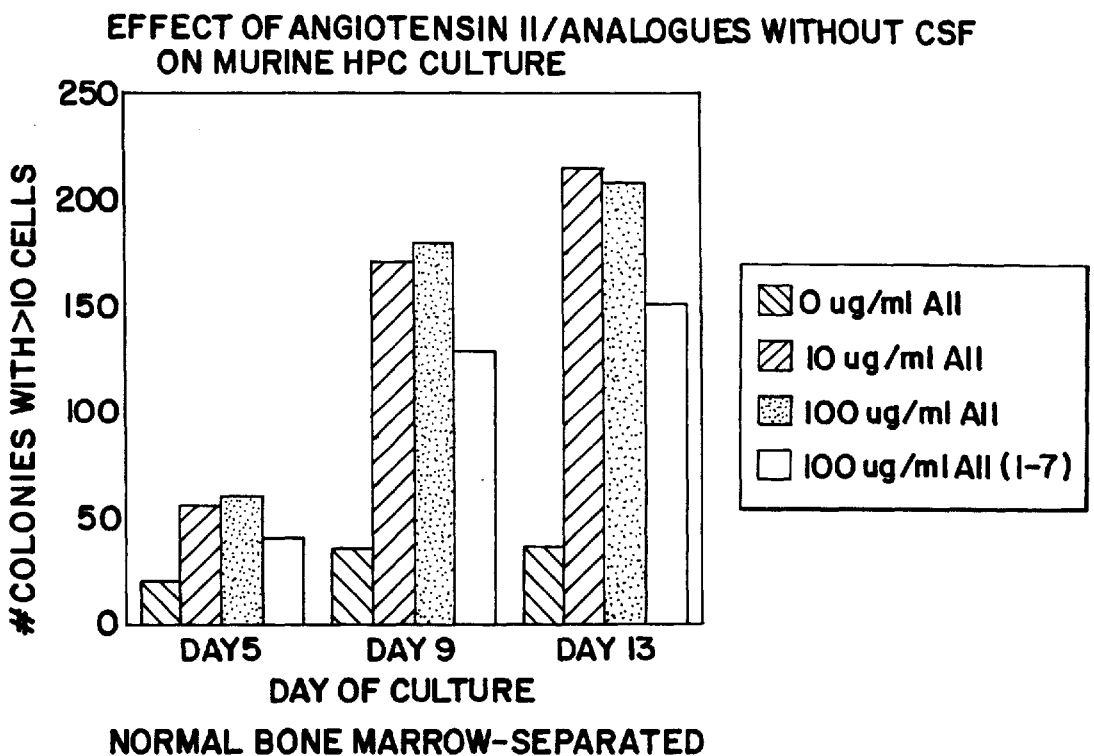
Figure 29:
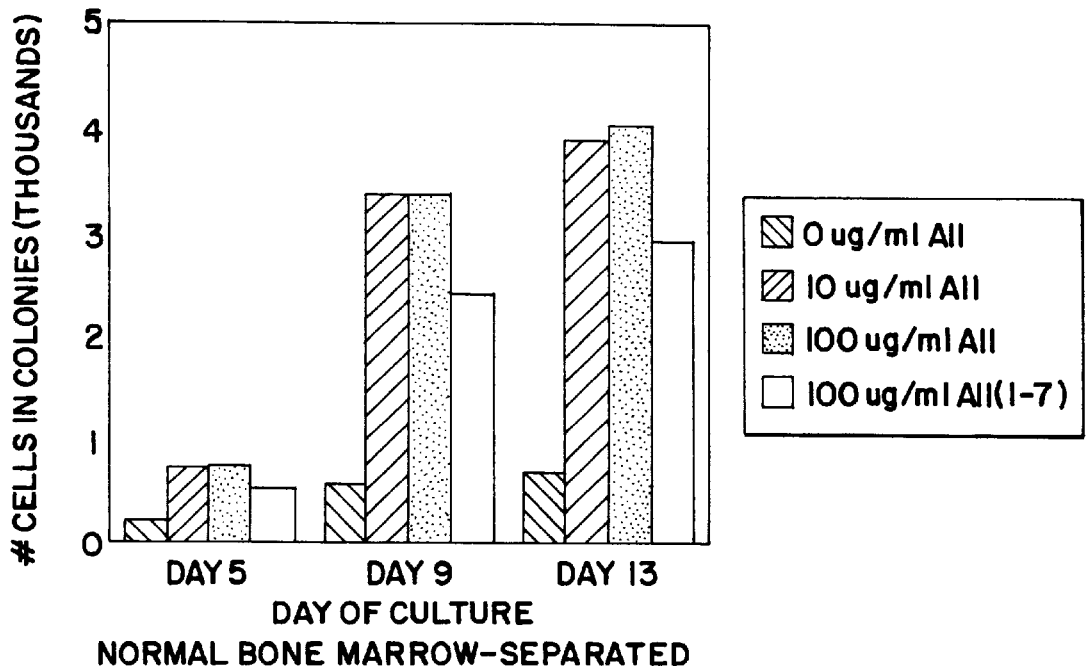
Figure 30:
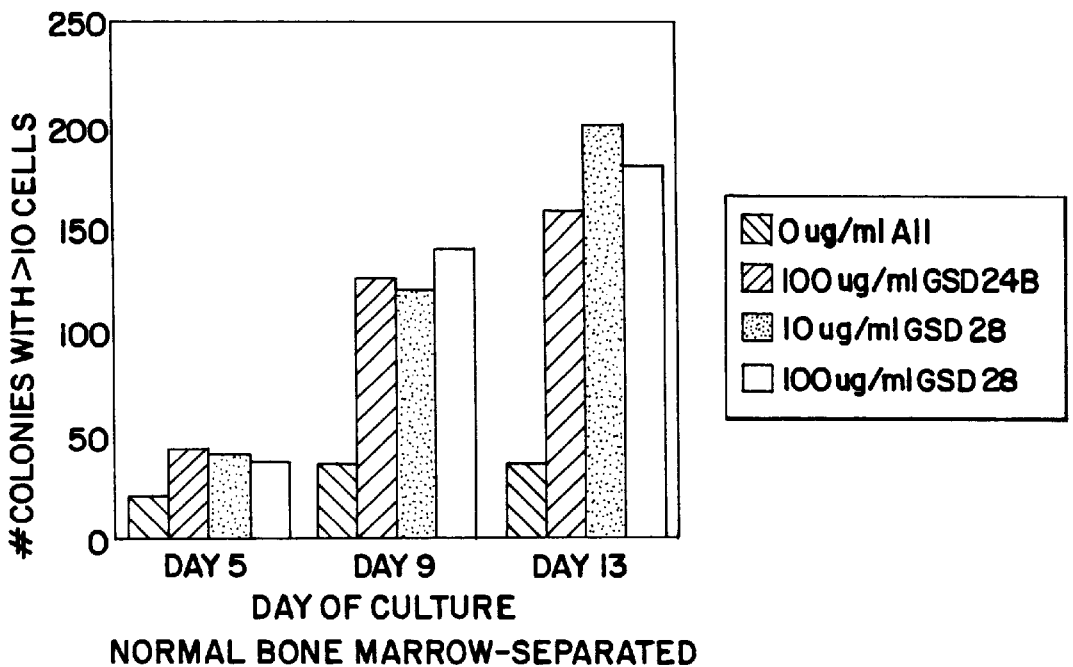
Figure 33:
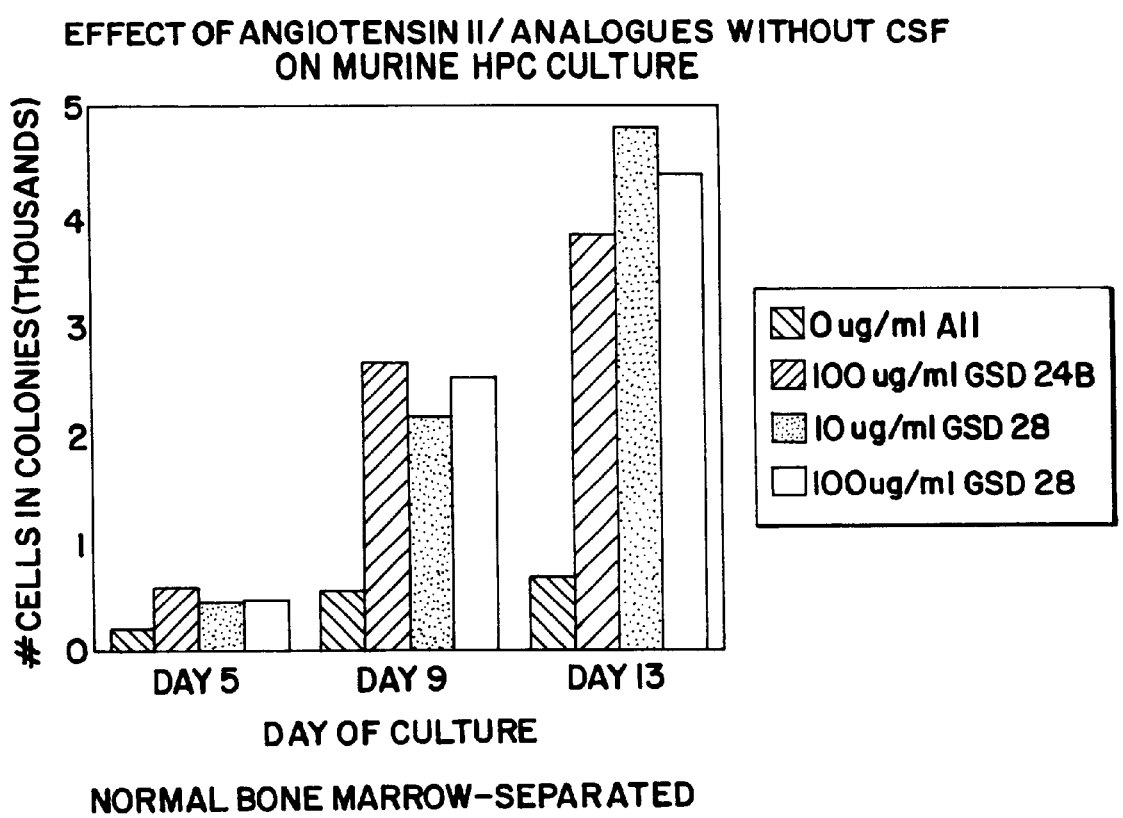

Bone marrow from female Sprague Dawley rats were harvested by flushing the femur with medium. The cells were placed in culture dishes 9 cm$^2$ in diameter, allowed to adhere overnight, and then placed in DMEM-LG medium containing antibiotics and 10% fetal calf serum together with varying concentrations of AII. At various times after culture initiation, the cells were washed with Tyrode's buffer and placed in osteogenic medium (DMEM-LG containing 10% fetal calf serum, 100 nM dexamethasone and 0.05 mM ascorbic acid) for 4 days prior to assessment of the level of alkaline phosphatase activity per well. Briefly, the wells were washed with Tyrode's buffer and 1 ml alkaline phosphatase substrate solution (50 mM glycine, pH 10.5, containing 1 mM magnesium chloride and 2.5 mM p-nitrophenyl phosphate) to each well. Fifteen minutes after addition of this aqueous substrate, the buffer was removed from the culture and mixed with 1 ml of 1N sodium hydroxide to stop the reaction. The absorbance of the resultant mixture at 405 nm was then determined via spectroscopy. The level of alkaline phosphatase activity is expressed as the level of absorbance per culture dish. These data are shown in FIG. 22 and demonstrate that AII can accelerate the proliferation of cells that express alkaline phosphatase when placed in medium appropriate to induce osteogenic differentiation.

EXAMPLE 8
Effect of Angiotensin II on Murine Lineage-specific Cells

HPC were harvested from C57B1/6 mice by immunomagnetic affinity chromatography and placed in semi-solid cultures with optimal growth medium in the absence of colony stimulating factors. At various times after initiation of culture, the formation of colonies and the size of the colonies (number of cells/colony) was assessed microscopically.

Female C57B1/6 mice were purchased from Simonson and used as a source of bone marrow cells in this study. The bone marrow was harvested from the femur and tibia of mice by flushing with phosphate buffered saline (PBS), pH 7.4, containing 2% fetal bovine serum (FBS) with a 21-gauge needle. The eluant from the flushing was centrifuged and the pellet was resuspended at $4 \times 10^7$ nucleated cells/ml in PBS containing PBS containing 2% FBS and 5% normal rat serum.

The reagents for immunomagnetic labeling were purchased from Stem Cell Technologies, Inc. (Vancouver, BC). Biotin-labeled monoclonal antibodies to the following murine lineage-specific cell surface antigens were included in a cocktail for HPC enrichment and used according to the manufacturer's instructions: CD5 (Ly-1), CD45-R (B220), CD11b (Mac-1), Myeloid Differentiation Antigen (Gr-1) and Erythroid Cells (TER 119). Ten μl of antibody cocktail was added to the bone marrow, mixed and allowed to incubate at 4° C. for 15 minutes. The cells were then resuspended at $4 \times 10^7$ cells/ml in PBS containing 2% FBS. The antibody cocktail was then washed out and 100 μl anti-biotin tetramer was added for each ml of cells. The suspension was mixed and incubated at 4° C. for 15 minutes. Sixty μl of magnetic colloid was then added for each ml of cells, the combination was mixed and incubated at 4° C. for 15 minutes to yield the immunomagnetically-labeled bone marrow cells.

A column containing a stainless steel matrix was prepared by washing the matrix with PBS followed by washing with PBS containing 2% protein. The immunomagnetically-labeled bone marrow cells were loaded onto the column and unlabeled cell-containing medium (enriched HPC) was collected in the flow through fraction at a flow rate of 0.2 ml/minute. Medium was added to the top of the column so that it did not run dry until 8 to 10 ml of enriched HPC were harvested. Approximately 2% of the cells loaded onto the column were isolated in the enriched HPC fractions.

The enriched HPC cell fractions were diluted into a semi-solid medium containing 0.9% methylcellulose in alpha minimal essential medium (alpha MEM), 30% fetal calf serum, 1% bovine serum albumin, $10^{-4}$ M 2-mercaptoethanol, 2 mM L-glutamine, and 2% conditioned medium. The conditioned medium was supernatant from splenocyte cultures (1×10⁶ cells/ml) incubated for 48 hours in RPMI 1640 containing 10 µg/ml pokeweed mitogen (PWM), 10% FCS, and antibiotics. Various concentrations of AII, between 0 and 100 µg/ml, or AII analogues or AII fragments were added in a small volume to the wells of microtiter dishes, which contained approximately either 3,000 cells per well or 30,000 cells per well. The cells were incubated at 37° C. and 5% $CO_2$ for 14 days. Microscopic evaluation of the cells was performed at various days after initiation of incubation, and the results are summarized in FIGS. 23–33. The results clearly demonstrate that HPC colony size increases proportionately with exposure to increased concentrations of AII, AII analogues and AII fragments, and thus that AII increases HPC proliferation in the absence of colony stimulating factors.

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

We claim:

1. A method of accelerating the proliferation of hematopoietic lineage-specific cells comprising contacting the cells with an amount effective to accelerate proliferation of the cells of at least one active agent comprising a sequence of at least seven contiguous amino acids of groups $R^1$–$R^8$ in the sequence of general formula I $$R^1-R^2-R^3-R^4-R^5-R^6-R^7-R^8$$

in which $R^1$ and $R^2$ together form a group of formula $$X-R^A-R^B-,$$

wherein X is H or a one to three peptide group, or is absent;

$R^A$ is selected from the group consisting of Asp, Glu, Asn, Acpc (1-aminocyclopentane carboxylic acid), Ala, Me$^2$Gly, Pro, Bet, Glu(NH$_2$), Gly, Asp(NH$_2$) and Suc, or $R^A$ is absent, $R^B$ is selected from the group consisting of Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO$_3$)$_2$, Thr, Ser, homoSer and azaTyr;

$R^5$ is selected from the group consisting of Ile, Ala, Leu, norLeu, Val and Gly;

$R^6$ is His, Arg or 6-NH$_2$-Phe;

$R^7$ is Pro or Ala; and $R^8$ is selected from the group consisting of Phe, Phe(Br), Ile, Tyr, or is absent, wherein the compound is not SEQ ID NO:1.

2. A method of accelerating the proliferation of hematopoietic pluripotent progenitor cells comprising contacting the cells with an amount effective to accelerate proliferation of the cells of at least one active agent comprising a sequence of at least seven contiguous amino acids of groups $R^1$–$R^8$ in the sequence of general formula I $$R^1-R^2-R^3-R^4-R^5-R^6-R^7-R^8$$

in which $R^1$ and $R^2$ together form a group of formula $$X-R^A-R^B-,$$

wherein X is H or a one to three peptide group, or is absent;

$R^A$ is selected from the group consisting of Asp, Glu, Asn, Acpc (1-aminocyclopentane carboxylic acid), Ala, Me$^2$Gly, Pro, Bet, Glu(NH$_2$), Gly, Asp(NH$_2$) and Suc, or $R^A$ is absent, $R^B$ is selected from the group consisting of Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO$_3$)$_2$, Thr, Ser, homoSer and azaTyr;

$R^5$ is selected from the group consisting of Ile, Ala, Leu, norLeu, Val and Gly;

$R^6$ is His, Arg or 6-NH$_2$-Phe;

$R^7$ is Pro or Ala;

$R^8$ is selected from the group consisting of Phe, Phe(Br), Ile, Tyr, or is absent; and wherein the compound is not SEQ ID NO:1.

3. The method of claim 1 or 2 wherein the active agent is selected from the group consisting of, SEQ ID NO:2, SEQ ID NO:3, SEQ ID NO:4, SEQ ID NO:12, SEQ ID NO:13, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, and SEQ ID NO:38.

4. The method of claims 1, 2, or 3 wherein the dosage of active agent is between about 0.1 ng/kg and about 1.0 mg/kg.

5. The method of claim 1, 2, or 3, wherein the concentration of active agent is between about 0.1 ng/ml and about 1.0 mg/ml.

6. The method of claim 1 or 2 wherein the active agent consists essentially of at least seven contiguous amino acids of groups $R^1$–$R^8$ in the sequence of general formula I.

7. The method of claim 6 wherein the dosage of active agent is between about 0.1 ng/kg and about 1.0 mg/kg.

8. The method of claim 6 wherein the concentration of active agent is between about 0.1 ng/ml and about 1.0 mg/ml.

9. A method of accelerating the differentiation of hematopoietic pluripotent progenitor or lineage-specific cells comprising contacting the cells with an amount effective to accelerate differentiation of the cells of at least one active agent comprising a sequence of at least seven contiguous amino acids of groups $R^1$–$R^8$ in the sequence of general formula I $$R^1-R^2-R^3-R^4-R^5-R^6-R^7-R^8$$

in which $R^1$ and $R^2$ together form a group of formula $$X-R^A-R^B-,$$

wherein X is H or a one to three peptide group, or is absent;

$R^A$ is selected from the group consisting of Asp, Glu, Asn, Acpc (1-aminocyclopentane carboxylic acid), Ala, $Me^2Gly$, Pro, Bet, Glu($NH_2$), Gly, Asp($NH_2$) and Suc, or $R^A$ is absent, $R^B$ is selected from the group consisting of Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr($PO_3$)$_2$, Thr, Ser, homoSer and azaTyr;

$R^5$ is selected from the group consisting of Ile, Ala, Leu, norLeu, Val and Gly;

$R^6$ is His, Arg or 6-$NH_2$-Phe;

$R^7$ is Pro or Ala; and $R^8$ is selected from the group consisting of Phe, Phe(Br), Ile, Tyr, or is absent; and, wherein the compound is not SEQ ID NO:1.

10. The method of claim 9 wherein the active agent is selected from the group consisting of SEQ ID NO:2, SEQ ID NO:3, SEQ ID NO:4, SEQ ID NO:12, SEQ ID NO:13, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, and SEQ ID NO:38.

11. The method of claim 9 or 10 wherein the hematopoietic pluripotent progenitor or lineage specific cells are selected from the group consisting of macrophages and monocytes.

12. The method of claim 9 or 10 wherein the dosage of active agent is between about 0.1 ng/kg and about 1.0 mg/kg.

13. The method of claim 9 or 10 wherein the concentration of active agent is between about 0.1 ng/ml and about 1.0 mg/ml.

* * * * *

UNITED STATES PATENT AND TRADEMARK OFFICE
CERTIFICATE OF CORRECTION

PATENT NO. : 6,335,195 B1
DATED : January 1, 2002
INVENTOR(S) : Kathleen E. Rodgers and Gere S. diZerega It is certified that error appears in the above-identified patent and that said Letters Patent is hereby corrected as shown below:

<u>Title page,</u>
Item [73], Assignee, should read as follows:

-- [73] Assignee: University of Southern California
Los Angeles, California --

Signed and Sealed this

Twentieth Day of April, 2004

JON W. DUDAS
*Acting Director of the United States Patent and Trademark Office*

SEQUENCE LISTING

```
<160> NUMBER OF SEQ ID NOS: 38

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
  1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:AII (2-8)

<400> SEQUENCE: 2

Arg Val Tyr Ile His Pro Phe
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)

<400> SEQUENCE: 4

Asp Arg Val Tyr Ile His Pro
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)
```

```
<400> SEQUENCE: 5

Arg Val Tyr Ile His Pro
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

Val Tyr Ile His Pro
  1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
  1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:AII (1-6)

<400> SEQUENCE: 8

Asp Arg Val Tyr Ile His
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10

Asp Arg Val Tyr
  1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)
```

```
<400> SEQUENCE: 11

Asp Arg Val
 1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (2)
<223> OTHER INFORMATION: Nle

<400> SEQUENCE: 12

Arg Xaa Tyr Ile His Pro Phe
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (4)
<223> OTHER INFORMATION: Nle

<400> SEQUENCE: 13

Arg Val Tyr Xaa His Pro Phe
 1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

His Pro Phe
 1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:AII analogue
      class
<220> FEATURE:
<221> NAME/KEY: UNSURE
<222> LOCATION: (1)
<223> OTHER INFORMATION: Xaa at position 1 can be Arg, Lys, Ala, Orn,
      Ser, MeGly, D-Arg, or D-Lys
```

```
<220> FEATURE:
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18

Arg Val Tyr Ala His Pro Phe
  1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII analogue
      1

<400> SEQUENCE: 19

Asp Arg Val Tyr Val His Pro Phe
  1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
  1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII analogue
      3
```

<400> SEQUENCE: 21

Ala Pro Gly Asp Arg Ile Tyr Val His Pro Phe
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue
      4

<400> SEQUENCE: 22

Glu Arg Val Tyr Ile His Pro Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue
      5

<400> SEQUENCE: 23

Asp Lys Val Tyr Ile His Pro Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:AII analogue
      6

<400> SEQUENCE: 24

Asp Arg Ala Tyr Ile His Pro Phe
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue
      7

<400> SEQUENCE: 25

Asp Arg Val Thr Ile His Pro Phe
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue
      8

<400> SEQUENCE: 26

Asp Arg Val Tyr Leu His Pro Phe
1               5

<210> SEQ ID NO 27
<211> LENGTH: 8
<212> TYPE: PRT

```
<213> ORGANISM: Artificial Sequence
<220> FEATURE:
<223> OTHER INFORMATION: Description of Artificial Sequence:AII analogue
      9

<400> SEQUENCE: 27

Asp Arg Val Tyr Ile Arg Pro Phe
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue
      10

<400> SEQUENCE: 28

Asp Arg Val Tyr Ile His Ala Phe
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue
      11

<400> SEQUENCE: 29

Asp Arg Val Tyr Ile His Pro Tyr
  1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII analogue
      12

<400> SEQUENCE: 30

Pro Arg Val Tyr Ile His Pro Phe
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII analogue
      14
<220> FEATURE:
<221> NAME/KEY: MOD_RES
<222> LOCATION: (4)
<223> OTHER INFORMATION: PHOSPHORYLATION
```

```
<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<220> FEATURE:
<221> NAME/KEY: MOD_RES
<222> LOCATION: (3)
<223> OTHER INFORMATION: Nle

<400> SEQUENCE: 33

Asp Arg Xaa Tyr Ile His Pro Phe
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<220> FEATURE:
<221> NAME/KEY: MOD_RES
<222> LOCATION: (5)
<223> OTHER INFORMATION: Nle

<400> SEQUENCE: 34

Asp Arg Val Tyr Xaa His Pro Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<220> FEATURE:
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence:
      p-aminophenylalanine 6 AII
<220> FEATURE:
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
 1               5
```

-continued

```
<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:angiotensin
      I

<400> SEQUENCE: 37

Asp Arg Val Tyr Ile His Pro Phe His Leu
 1               5                  10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:GSD 28:
      Ile8-AII

<400> SEQUENCE: 38

Asp Arg Val Tyr Ile His Pro Ile
 1               5
```